United States Patent
Khine et al.

(10) Patent No.: US 12,083,207 B2
(45) Date of Patent: *Sep. 10, 2024

(54) COSMETIC COMPOSITIONS, KITS THEREOF, AND METHODS FOR MAKING AND USING THE SAME

(71) Applicant: L'OREAL, Paris (FR)

(72) Inventors: Cho-Cho Khine, Bridgewater, NJ (US); Ronak Rughani, Edison, NJ (US)

(73) Assignee: L'OREAL, Paris (FR)

( * ) Notice: Subject to any disclaimer, the term of this patent is extended or adjusted under 35 U.S.C. 154(b) by 250 days.

This patent is subject to a terminal disclaimer.

(21) Appl. No.: 17/007,752

(22) Filed: Aug. 31, 2020

(65) Prior Publication Data
US 2022/0062135 A1    Mar. 3, 2022

(51) Int. Cl.
| A61K 8/42 | (2006.01) |
| A61K 8/34 | (2006.01) |
| A61K 8/362 | (2006.01) |
| A61K 8/92 | (2006.01) |
| A61Q 5/12 | (2006.01) |

(52) U.S. Cl.
CPC ............ *A61K 8/42* (2013.01); *A61K 8/345* (2013.01); *A61K 8/362* (2013.01); *A61K 8/92* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 2,987,446 A | 6/1961 | Riethmuller | |
| 5,993,837 A * | 11/1999 | Calello | A61K 8/42 514/937 |
| 10,137,073 B2 | 11/2018 | De Lemos et al. | |
| 2002/0019547 A1 | 2/2002 | Tuloup et al. | |
| 2002/0081271 A1 | 6/2002 | Martin et al. | |
| 2002/0137795 A1 | 9/2002 | Martin et al. | |
| 2003/0224060 A1 | 12/2003 | Simonnet et al. | |
| 2004/0202688 A1 * | 10/2004 | Mougin | A61Q 3/02 424/401 |
| 2005/0113269 A1 * | 5/2005 | Landa | A61Q 5/06 510/130 |
| 2007/0225360 A1 | 9/2007 | Pinnell et al. | |
| 2007/0274926 A1 * | 11/2007 | Fuls | A01N 37/04 514/553 |
| 2008/0118449 A1 | 5/2008 | Ronlan | |
| 2008/0160110 A1 | 7/2008 | Kang et al. | |
| 2009/0286874 A1 | 11/2009 | Pinnell et al. | |
| 2013/0115173 A1 * | 5/2013 | Trumbore | A61K 9/122 424/45 |
| 2014/0364509 A1 * | 12/2014 | Wegner | A61K 8/678 514/724 |
| 2020/0069025 A1 | 3/2020 | Ferebee Maher et al. | |
| 2020/0129405 A1 | 4/2020 | Mitchell et al. | |

FOREIGN PATENT DOCUMENTS

| | | | | |
|---|---|---|---|---|
| CA | 3107391 A1 | | 2/2020 | |
| CN | 105287251 | * | 2/2016 | ............ A61Q 3/02 |
| CN | 106176454 A | | 12/2016 | |
| EP | 1535607 A1 | | 6/2005 | |
| EP | 1702610 A1 | | 9/2006 | |
| FR | 3046352 A1 | * | 7/2017 | .......... A61K 36/185 |
| KR | 20110044844 A | | 5/2011 | |
| WO | 2007054833 A2 | | 5/2007 | |
| WO | WO-2011098216 A1 | * | 8/2011 | ............ A61K 8/02 |

OTHER PUBLICATIONS

Safety Assessment of Hydroxyethyl Urea. https://www.cir-safety.org/sites/default/files/hyurea092018TR.pdf. Published: Oct. 5, 2018.*
WO2011098216 Eng Tran. Published: Aug. 18, 2011. (Year: 2011).*
CN105287251 Eng Tran. Published: Feb. 3, 2016. (Year: 2016).*
8 Ingredients. https://www.naturallycurly.com/curlreading/ingredients/8-ingredients-that-arent-nearly-as-creepy-as-their-names. Published. Aug. 29, 2014 (Year: 2014).*
Bafti. J. Chem. Sci. vol. 126, No. 3, May 2014, pp. 881-887. (Year: 2014).*
FR3046352 Eng Tran. Published: Jul. 7, 2017. (Year: 2017).*
International Search Report and Written Opinion issued on Dec. 22, 2021 for corresponding PCT Application No. PCT/US2021/047086.
Preliminary Search Report and Written Opinion issued on Jul. 6, 2021 for corresponding French Application No. FR2010605.

* cited by examiner

*Primary Examiner* — David J Blanchard
*Assistant Examiner* — Lori K Mattison
(74) *Attorney, Agent, or Firm* — POLSINELLI PC

(57) ABSTRACT

Cosmetic compositions, kits thereof, and methods of making and using such cosmetic compositions. The cosmetic compositions comprising about 0.1 to about 25 wt. % of citric acid, about 0.2 to about 40 wt. % of one or more urea compound, and about 20 wt. % or more water wherein all weight percentages are based on the total weight of the cosmetic composition. Additionally, the cosmetic compositions are typically formulated to have a molar ratio of the citric acid of (a) to the urea compound of (b) is 1 or less.

11 Claims, 8 Drawing Sheets

COSMETIC COMPOSITIONS, KITS THEREOF, AND METHODS FOR MAKING AND USING THE SAME

FIELD OF THE DISCLOSURE

The present disclosure relates to cosmetic compositions and kits thereof. Aspects of the present disclosure also relate to methods for making such cosmetic compositions and methods of using such cosmetic compositions.

BACKGROUND

Consumers desire new and improved compositions for treating, caring for, and/or conditioning keratinous substances, such as skin or hair. Hair and skin are exposed to intrinsic and extrinsic influences such as environmental factors, mechanical factors, chemical factors, heat, and aging.

For example, the action of external atmospheric agents such as light and bad weather, and also by heat, mechanical or chemical treatments, such as brushing, combing, dyeing, bleaching, permanent-waving and/or relaxing, blow-drying, flat ironing, or even repeated washing can damage and weaken hair fibers. Over time, hair may become dry, coarse, brittle or dull, especially in fragile areas, and more particularly at the ends, resulting in split ends.

Thus, to overcome these drawbacks, it is common practice to resort to haircare products using compositions intended to condition the hair, giving it satisfactory cosmetic properties, especially in terms of smoothness, sheen, softness, suppleness, lightness, a natural feel and good disentangling properties. For example, hair care compositions, such as hair conditioner and/or treatment compositions, may be used before or after the hair has been washed with shampoo and/or subjected to a chemical treatment in order to improve or return to the hair its natural luster, shine, and softness, or to improve the feel, appearance, and manageability of hair.

It is understood that different forms of haircare and skin care compositions can provide different benefits.

However, there is still a need for providing improved hair manageability, for example, improved hair alignment, reduced unwanted volume (especially reduced frizz), and increased shine. There is also a need to develop cosmetic products that can impart other benefits at the same time in addition to caring and conditioning benefits, such as styling, volume, shaping, curl definition (for curly or wavy hair), and restylability or reshaping (without the need to reapply the product).

SUMMARY OF THE DISCLOSURE

Aspects of the present disclosure relate to cosmetic compositions and kits thereof. Further aspects of the present disclosure relate to methods for making such cosmetic compositions and methods of using such cosmetic compositions.

The cosmetic compositions disclosed herein advantageously provide increased durability and/or strength, perceivable visual shine, fiber alignment, reduced frizz, and/or increased hair manageability. Without being limited to any specific theories, the inventors believe that the cosmetic compositions, and particularly cosmetic compositions containing certain deep eutectic solvent systems, may diffuse into the hair and form an extensive network. The extensive network may reinforce and/or stabilize the hair structure, which will ultimately reduce hair frizz associated with high humidity.

Additionally, the cosmetic compositions may be capable of self-association typically through hydrogen bond interactions, which may enable the cosmetic compositions to reinforce and/or strengthen hair, particularly damaged hair. In some embodiments, cosmetic compositions restore damaged hair. The inventors were also surprised to discover that the cosmetic compositions may increase the straightness of the hair without the use of heat, such as from an iron, blow dryer, or the like.

The cosmetic compositions typically include:
 (a) about 0.1 to about 25 wt. % of citric acid;
 (b) about 0.2 to about 40 wt. % of one or more urea compound,
    wherein a weight ratio of the citric acid of (a) to the urea compound of (b) is 1 or less; and
 (c) about 20 wt. % or more water, (c)
    wherein all weight percentages are based on the total weight of the cosmetic composition.

The cosmetic composition may include an amount of deep eutectic solvent. Preferably, the amount of the deep eutectic solvent is 1 wt. % or more. The deep eutectic solvent may comprise the urea compound of (a) and citric acid of (b).

Preferably, the urea compound of is chosen from dimethyl urea, a hydroxyl ethyl urea, urea, and a mixture thereof. In some cases, the weight ratio of the citric acid of (a) to the urea compound of (b) is about 1:1 to 1:8. In further cases, the weight ratio of the citric acid of (a) to the urea compound of (b) is about 1:1 to 1:6.

In at least one embodiment, the cosmetic composition includes about 2.5 to about 40 wt. % of the one or more urea compound and about 1.5 to about 25 wt. % of the citric acid. In at least one other embodiment, the cosmetic composition includes about 20 to about 40 wt. % of the one or more urea compound and about 15 to about 25 wt. % of the citric acid.

The cosmetic compositions may further include about 0.1 to about 10 wt. % of one or more cationic surfactant. The one or more cationic surfactant may be chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

In some cases, the cosmetic compositions include about 0.1 to about 25 wt. % of one or more fatty compounds. The fatty compound may be chosen from a fatty alcohol, a fatty ester, a fatty ether, a fatty acid, a wax, an oil, a derivative thereof, and a mixture thereof.

Additionally or alternatively, the cosmetic compositions may include about 20 to about 95 wt. % of a polyol. Suitable polyols include ethylene glycol, propylene glycol, butylene glycol, hexylene glycol, pentylene glycol, diethylene glycol, dipropylene glycol, 1,3 propanediol, glycerin, polyethylene glycols, or a mixture thereof.

The cosmetic compositions may include about 0.1 to about 20 wt. % of a thickening agent. The thickening agent may be chosen from polyacrylate crosspolymers or crosslinked polyacrylate polymers, cationic acrylate copolymers, anionic acrylic or carboxylic acid polymers, polyacrylamide polymers, polysaccharides, gums, polyquaterniums, vinylpyrrolidone homopolymers/copolymers, $C_{8-24}$ hydroxyl substituted aliphatic acid, $C_{8-24}$ conjugated aliphatic acid, sugar fatty esters, polyglyceryl esters, and a mixture thereof.

Aspects of the disclosure relate to methods for producing cosmetic compositions. The methods for producing cosmetic compositions typically include:
(I) producing a deep eutectic solvent system comprising:
  (a) about 0.1 to about 25 wt. % of citric acid; and
  (b) about 0.2 to about 40 wt. % of one or more urea compound chosen from dimethyl urea, a hydroxyl ethyl urea, or a combination thereof,
    wherein a weight ratio of the citric acid of (a) to the urea compound of (b) is 1 or less; and
(II) adding the deep eutectic solvent system of (I) to a base composition to produce a cosmetic composition.

The method may further include the step of mixing the citric acid of (a) and the urea compound of (b) and, optionally, heating the citric acid of (a) and the urea compound of (b) to a temperature of about 70° C. to about 90° C.

Further aspects of the disclosure relate to cosmetic compositions prepared by the methods for producing cosmetic compositions disclosed herein.

In accordance with a further aspect, provided are methods for treating hair. The method for treating hair typically comprise:
(I) optionally, applying a shampoo to hair;
(II) optionally, rinsing the hair to remove at least a portion of the shampoo;
(III) applying a cosmetic composition comprising:
  (a) about 0.1 to about 25 wt. % of citric acid; and
  (b) about 0.2 to about 40 wt. % of one or more urea compound chosen from dimethyl urea, a hydroxyl ethyl urea, or a combination thereof,
    wherein a weight ratio of the citric acid of (a) to the urea compound of (b) is 1 or less; and
(IV) optionally, rinsing the hair to remove at least a portion of the cosmetic composition.

BRIEF DESCRIPTION OF THE DRAWINGS

Implementation of the present technology will now be described, by way of example only, with reference to the attached figures, wherein.

Figure 1:
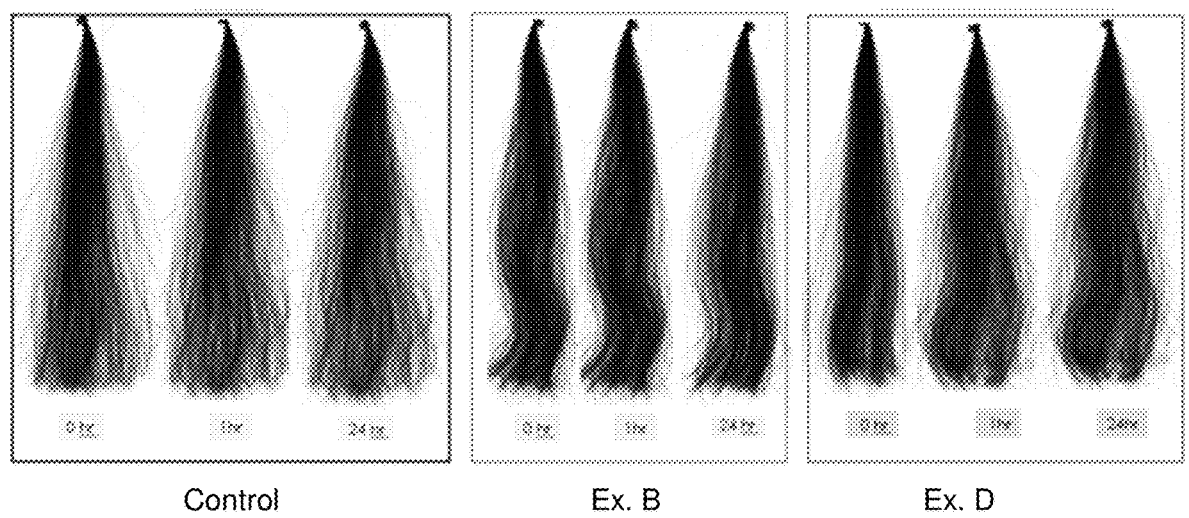
FIGS. 1 and 2 are pictures of hair swatches treated with compositions according to the instant disclosure and subjected to humidity in accordance with aspects of the disclosure.

It should be understood that the various aspects are not limited to the arrangements and instrumentality shown in the drawings.

DETAILED DESCRIPTION OF THE DISCLOSURE

Aspects of the present disclosure relate to cosmetic compositions and kits thereof. Further aspects of the present disclosure relate to methods for making such cosmetic compositions and methods of using such cosmetic compositions. The cosmetic compositions disclosed herein advantageously provide increased durability and/or strength, perceivable visual shine, fiber alignment, reduced frizz, and/or increased hair manageability.

The inventors surprisingly discovered that certain compounds in specific ratios enables the cosmetic compositions to provide improved durability and strength in conjunction with a reduction of hair frizz. Without being limited to any specific theories, the inventors believe that the cosmetic compositions, and particularly cosmetic compositions containing certain deep eutectic solvent (DES) systems, may diffuse into the hair and form an extensive network. The extensive network may reinforce and/or stabilize the hair structure, which will ultimately reduce hair frizz associated with high humidity.

The cosmetic compositions and/or their ingredients may be capable of self-association typically through non-covalent interactions (i.e., hydrogen bond, ionic and Van Der Waal interactions), which may enable the cosmetic compositions to reinforce and/or strengthen hair, particularly damaged hair. In some embodiments, cosmetic compositions restore damaged hair. Additionally, the inventors surprisingly discovered that such cosmetic compositions may increase the straightness/alignment of the hair fibers without the use of heat, such as from an iron, blow dryer, or the like. The cosmetic compositions, such as those containing a DES system, have also shown evidence of shine benefits which are being currently investigated The cosmetic compositions according to an aspect of the disclosure typically include:
(a) about 0.1 to about 25 wt. % of citric acid;
(b) about 0.2 to about 40 wt. % of one or more urea compound, wherein a weight ratio of the citric acid of (a) to the urea compound of (b) is 1 or less; and
(c) about 20 wt. % or more water,
  wherein all weight percentages are based on the total weight of the cosmetic composition.

The cosmetic compositions may include an amount of a deep eutectic solvent system ("DES"). In some cases, the amount of the deep eutectic solvent is about 1 wt. % or more, preferably about 2 wt. % or more, about 3 wt. % or more, about 4 wt. % or more, about 5 wt. % or more, about 6 wt. % or more, about 7 wt. % or more, about 8 wt. % or more, about 9 wt. % or more, about 10 wt. % or more, about 12 wt. % or more, about 14 wt. % or more, about 16 wt. % or more, about 18 wt. % or more, about 20 wt. % or more, about 22 wt. % or more, about 24 wt. % or more, about 26 wt. % or more, about 28 wt. % or more, about 30 wt. % or more, about 32 wt. % or more, about 34 wt. % or more, about 36 wt. % or more, about 40 wt. % or more, about 45 wt. % or more, about 50 wt. % or more, or about 60 wt. % or more, based on the total weight of the cosmetic composition.

The cosmetic composition may be formulated to have a weight ratio of the citric acid of (i) to the urea compound of (ii) may be about 10:1 to about 2:10. In some instances, the cosmetic composition may be formulated to have a weight ratio of citric acid to urea compound(s) of about 10:1 to about 0.5:10, about 9:1 to about 0.5:10, about 8:1 to about 0.5:10, about 7:1 to about 0.5:10, about 6:1 to about 0.5:10, about 5:1 to about 0.5:10, about 4:1 to about 0.5:10, about 3:1 to about 0.5:10; 10:1 to about 1:10, about 9:1 to about 1:10, about 8:1 to about 1:10, about 7:1 to about 1:10, about 6:1 to about 1:10, about 5:1 to about 1:10, about 4:1 to about 1:10, about 3:1 to about 1:10; 10:1 to about 2:10, about 9:1 to about 2:10, about 8:1 to about 2:10, about 7:1 to about 2:10, about 6:1 to about 2:10, about 5:1 to about 2:10, about 4:1 to about 2:10, about 3:1 to about 2:10; about 10:1 to about 2:8, about 9:1 to about 2:8, about 8:1 to about 2:8, about 7:1 to about 2:8, about 6:1 to about 2:8, about 5:1 to about 2:8, about 4:1 to about 2:8, about 3:1 to about 2:8; about 10:1 to about 2:6, about 9:1 to about 2:6, about 8:1 to about 2:6, about 7:1 to about 2:6, about 6:1 to about 2:6, about 5:1 to about 2:6, about 4:1 to about 2:6, about 3:1 to about 2:6; about 3:1 to about 1:10, about 3:1 to about 1:9, about 3:1 to about 1:8, about 3:1 to about 1:7, about 3:1 to about 1:6, about 3:1 to about 2:10, about 3:1 to about 2:9, about 3:1 to about 2:8, about 3:1 to about 2:7, about 3:1 to about 2:6, about 3:1 to about 2:5, about 3:1 to about 2:4, or about 3:1 to about 2:3, about 2:1 to about 2:10, about 1:1 to about 2:10, about 3:1 to about 2:9, about 3:1 to about 2:8, about 3:1 to about 2:7, about 3:1 to about 2:6, about 3:1 to about 2:5, about 3:1 to about 2:4, or about 3:1 to about 2:3 including ranges and sub-ranges there between (e.g., about 3:1 to about 2:5, about 2:1 to about 2:5, about 1:1 to about 2:5, about 1:1 to about 2:4, etc.).

The cosmetic composition may be formulated to have a molar ratio of the citric acid of (i) to the urea compound of (ii) may be about 10:1 to about 0.5:10. In some instances, the cosmetic composition may be formulated to have a weight ratio of citric acid to urea compound(s) of 10:1 to about 0.5:10, about 9:1 to about 0.5:10, about 8:1 to about 0.5:10, about 7:1 to about 0.5:10, about 6:1 to about 0.5:10, about 5:1 to about 0.5:10, about 4:1 to about 0.5:10, about 3:1 to about 0.5:10; 10:1 to about 1:10, about 9:1 to about 1:10, about 8:1 to about 1:10, about 7:1 to about 1:10, about 6:1 to about 1:10, about 5:1 to about 1:10, about 4:1 to about 1:10, about 3:1 to about 1:10; about 10:1 to about 2:10, about 9:1 to about 2:10, about 8:1 to about 2:10, about 7:1 to about 2:10, about 6:1 to about 2:10, about 5:1 to about 2:10, about 4:1 to about 2:10, about 3:1 to about 2:10; about 10:1 to about 2:8, about 9:1 to about 2:8, about 8:1 to about 2:8, about 7:1 to about 2:8, about 6:1 to about 2:8, about 5:1 to about 2:8, about 4:1 to about 2:8, about 3:1 to about 2:8; about 10:1 to about 2:6, about 9:1 to about 2:6, about 8:1 to about 2:6, about 7:1 to about 2:6, about 6:1 to about 2:6, about 5:1 to about 2:6, about 4:1 to about 2:6, about 3:2 to about 2:6; about 2:1 to about 2:10, about 1:1 to about 2:10, about 3:2 to about 2:9, about 3:2 to about 2:8, about 3:2 to about 2:7, about 3:2 to about 2:6, about 3:2 to about 2:5, about 3:2 to about 2:4, about 3:2 to about 2:3, about 1:1 to about 1:4, about 1:1 to about 1:3, about 1:1 to about 1:2, or about 1:1.3 to about 1:1.6, including ranges and sub-ranges therebetween (e.g., about 3:2 to about 2:5, about 2:1 to about 2:5, about 1:1 to about 2:5, about 1:1 to about 2:4, etc.).

Preferably, the DES system comprises citric acid and one or more urea compound. In some cases, the DES system is formed from citric acid and one or more urea compound, such as those chosen from dimethyl urea, a hydroxyl ethyl urea, urea, and a mixture thereof.

Additionally or alternatively, the combination of the citric acid and the urea compound(s) is in the form of a DES system before inclusion into the base of the cosmetic composition. The base of the cosmetic composition may be a composition of one or more components of the cosmetic composition. For example, in some instances, the base composition may include all components of the cosmetic composition except for the citric acid and urea compound(s). The cosmetic composition may at least partially include the DES system after the DES system is incorporated into the base cosmetic composition.

Additionally or alternatively, the cosmetic composition may include arginine. In some cases, the arginine is l-arginine, d-arginine, and/or may be in a racemic mixture.

Suitable components, such as those listed below, may be included or excluded from the formulations for the cosmetic compositions depending on the specific combination of other components, the form of the cosmetic compositions, and/or the use of the formulation (e.g., an aqueous solution, a lotion, gel, cream, spray, etc.). The cosmetic compositions may be formulated as a hair care composition and/or a hair cosmetic composition and/or a hair treatment composition and/or a skin care composition and/or scalp care composition, e.g., for use on the hair and/or skin.

Citric Acid

The cosmetic compositions include citric acid typically in an amount of about 0.1 to about 25 wt. %, based on the total weight of the cosmetic composition. For instance, the amount of citric acid present in the cosmetic composition may be about 0.1 to about 25 wt. %, about 0.1 to about 22 wt. %, about 0.1 to about 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 25 wt. %, about 0.5 to about 22 wt. %, about 0.5 to about 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 25 wt. %, about 1 to about 22 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; about 3 to about 25 wt. %, about 1 to about 22 wt. %, about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 9 wt. %, about 3 to about 8 wt. %, about 3 to about 7 wt. %, about 3 to about 6 wt. %, about 3 to about 5 wt. %; about 5 to about 25 wt. %, about 5 to about 22 wt. %, about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 9 wt.

%, about 5 to about 8 wt. %, about 5 to about 7 wt. %; about 10 to about 25 wt. %, about 10 to about 22 wt. %, about 10 to about 20 wt. %, about 10 to about 18 wt. %, about 10 to about 16 wt. %, about 10 to about 14 wt. %, about 10 to about 12 wt. %; about 15 to about 25 wt. %, about 15 to about 22 wt. %, about 15 to about 20 wt. %, about 15 to about 18 wt. %; about 20 to about 25 wt. %, or about 20 to about 22 wt. %, including ranges and subranges thereof, based on the total weight of the cosmetic composition.

Urea Compound(s)

The cosmetic compositions include one or more urea compound(s) typically in an amount of about 0.2 to about 40 wt. %, based on the total weight of the cosmetic composition. For instance, the amount of the one or more urea compound(s) present in the cosmetic composition may be about 0.2 to about 35 wt. %, about 0.2 to about 32 wt. %, about 0.2 to about 30 wt. %, about 0.2 to about 28 wt. %, about 0.2 to about 26 wt. %, about 0.2 to about 24 wt. %, about 0.2 to about 22 wt. %, about 0.2 to about 20 wt. %, about 0.2 to about 18 wt. %, about 0.2 to about 16 wt. %, about 0.2 to about 14 wt. %, about 0.2 to about 12 wt. %, about 0.2 to about 10 wt. %, about 0.2 to about 9 wt. %, about 0.2 to about 8 wt. %, about 0.2 to about 7 wt. %, about 0.2 to about 6 wt. %, about 0.2 to about 5 wt. %, about 0.2 to about 4 wt. %, about 0.2 to about 3 wt. %, about 0.2 to about 2 wt. %, about 0.2 to about 1 wt. %; about 0.5 to about 40 wt. %, about 0.5 to about 35 wt. %, about 0.5 to about 32 wt. %, about 0.5 to about 30 wt. %, about 0.5 to about 28 wt. %, about 0.5 to about 26 wt. %, about 0.5 to about 24 wt. %, about 0.5 to about 22 wt. %, about 0.5 to about 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 40 wt. %, about 1 to about 35 wt. %, about 1 to about 32 wt. %, about 1 to about 30 wt. %, about 1 to about 28 wt. %, about 1 to about 26 wt. %, about 1 to about 24 wt. %, about 1 to about 22 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; about 3 to about 40 wt. %, about 3 to about 35 wt. %, about 3 to about 32 wt. %, about 3 to about 30 wt. %, about 3 to about 28 wt. %, about 3 to about 26 wt. %, about 3 to about 24 wt. %, about 3 to about 22 wt. %, about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 9 wt. %, about 3 to about 8 wt. %, about 3 to about 7 wt. %, about 3 to about 6 wt. %, about 3 to about 5 wt. %; about 5 to about 40 wt. %, about 5 to about 35 wt. %, about 5 to about 32 wt. %, about 5 to about 30 wt. %, about 5 to about 28 wt. %, about 5 to about 26 wt. %, about 5 to about 24 wt. %, about 5 to about 22 wt. %, about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 9 wt. %, about 5 to about 8 wt. %, about 5 to about 7 wt. %; about 10 to about 40 wt. %, about 10 to about 35 wt. %, about 10 to about 32 wt. %, about 10 to about 30 wt. %, about 10 to about 28 wt. %, about 10 to about 26 wt. %, about 10 to about 24 wt. %, about 10 to about 22 wt. %, about 10 to about 20 wt. %, about 10 to about 18 wt. %, about 10 to about 16 wt. %, about 10 to about 14 wt. %, about 10 to about 12 wt. %; about 15 to about 40 wt. %, about 15 to about 35 wt. %, about 15 to about 32 wt. %, about 15 to about 30 wt. %, about 15 to about 28 wt. %, about 15 to about 26 wt. %, about 15 to about 24 wt. %, about 15 to about 22 wt. %, about 15 to about 20 wt. %, about 15 to about 18 wt. %; about 20 to about 40 wt. %, about 20 to about 35 wt. %, about 20 to about 32 wt. %, about 20 to about 30 wt. %, about 20 to about 28 wt. %, about 20 to about 26 wt. %, about 20 to about 24 wt. %; about 25 to about 40 wt. %, about 25 to about 35 wt. %, about 25 to about 32 wt. %, about 25 to about 30 wt. %; about 30 to about 40 wt. %, or about 30 to about 35 wt. %, including ranges and subranges thereof, based on the total weight of the cosmetic composition.

The urea compounds may have a structure in accordance with the following formula:

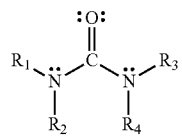

wherein $R_1$, $R_2$, $R_3$, and $R_4$ are independently selected from hydrogens, $C_4$ to $C_{10}$ unsubstituted aryl, $C_4$ to $C_{10}$ substituted aryl, $C_2$ to $C_{10}$ unsubstituted heterocycle, $C_2$ to $C_{10}$ substituted heterocycle, $C_1$ to $C_{10}$ unsubstituted alkyl, $C_1$ to $C_{10}$ substituted alkyl, $C_3$-$C_{10}$ unsubstituted cycloalkyl, and $C_3$-$C_{10}$ substituted cycloalkyl.

The urea compounds are preferably chosen from is dimethyl urea, a hydroxyethyl urea, urea or mixtures thereof. Non-limiting examples of urea compounds include urea, urea derivatives, imidazolidinyl urea, diazolidinyl urea, m-dimethylaminophenyl urea, dimethyl urea, a hydroxyethyl urea, N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(tris-hydroxymethylmethyl)urea; N-ethyl-N'-(2-hydroxyethyl)urea; N,N-bis(2-hydroxyethyl)urea; N,N'-bis(2-hydroxyethyl)urea; N,N-bis(2-hydroxypropyl)urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl).-N',N'-dimethylurea; N,N,N',N'-tetrakis(2-hydroxyethyl)urea; N',N'-bis(2-hydroxyethyl)-N', and N'-bis(2-hydroxypropyl)-urea.

Water

The total amount of water in the cosmetic composition can vary, but is typically about 20 wt. % or more based on the total weight of the cosmetic composition. In some instances, total amount of water is about 20 to about 99 wt. %, about 20 to about 95 wt. %, about 20 to about 90 wt. %, about 20 to about 80 wt. %, about 20 to about 70 wt. %, about 20 to about 60 wt. %, about 20 to about 50 wt. %, about 20 to about 40 wt. %; about 30 to about 99 wt. %, about 30 to about 95 wt. %, about 30 to about 90 wt. %, about 30 to about 80 wt. %, about 30 to about 70 wt. %, about 30 to about 60 wt. %, about 30 to about 50 wt. %, about 30 to about 40 wt. %; about 40 to about 99 wt. %, about 40 to about 95 wt. %, about 40 to about 90 wt. %, about 40 to about 80 wt. %, about 40 to about 70 wt. %, about 40 to about 60 wt. %, about 40 to about 50 wt. %; about 50 to about 99 wt. %, about 50 to about 95 wt. %, about 50 to about 90 wt. %, about 50 to about 80 wt. %, about 50 to about 70 wt. %, about 50 to about 60 wt. %; about 60 to about 99 wt. %, about 60 to about 95 wt. %, about 60 to about 90 wt. %, about 60 to about 80 wt. %, about 60 to about 70 wt. %; about 70 to about 99 wt. %, about 70 to about 95 wt. %, about 70 to about 90 wt. %, about 70 to about 80 wt. %; about 80 to about 99 wt. %, about 80 to about 95 wt. %, about 80 to about 90 wt. %; about 90 to about 99 wt. %, about 90 to about 95 wt. %; or about 95 to about 99 wt. %, including ranges and subranges therebetween, based on the total weight of the cosmetic composition.

Cationic Surfactant(s)

The cosmetic composition may, optionally, include a cationic surfactant(s). The amount of cationic surfactant(s) may be from about 0.1 to about 10 wt. % of the total weight of the cosmetic composition. In some instances, the cationic surfactant(s) are in an amount ranging from about 0.1 to about 10 wt. %, about 0.1 to about 8 wt. %, about 0.1 to about 6 wt. %, about 0.1 to about 4 wt. %, about 0.1 to about 3 wt. %; about 0.2 to about 10 wt. %, about 0.2 to about 8 wt. %, about 0.2 to about 6 wt. %, about 0.2 to about 4 wt. %, about 0.2 to about 3 wt. %; about 0.5 to about 10 wt. %, about 0.5 to about 8 wt. %, about 0.5 to about 6 wt. %, about 0.5 to about 4 wt. %, about 0.5 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including ranges and sub-ranges therebetween, based on the total weight of the cosmetic composition.

In certain embodiments, the cationic surfactants include or are chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

Additional, non-limiting examples of cationic surfactants include behenalkonium chloride, benzethonium chloride, cetylpyridinium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and mixtures thereof.

The cationic surfactant(s) may also be chosen from optionally polyoxyalkylenated, primary, secondary or tertiary fatty amines, or salts thereof, and quaternary ammonium salts, and mixtures thereof. In some cases it is useful to use salts such as chloride salts of the quaternary ammonium compounds.

The fatty amines generally comprise at least one $C_8$-$C_{30}$ hydrocarbon-based chain. For example, quaternary ammonium salts, which may be incorporated in certain instances, include those corresponding to the following general formula:

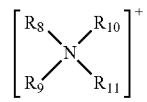

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts having a structure in accordance with the above general formula (III), those that are preferred are, on the one hand, tetraalkylammonium salts, for instance dialkyldimethylammonium or alkyltrimethylammonium salts in which the alkyl group contains approximately from 12 to 22 carbon atoms, such as behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

Examples of quaternary ammonium salt of imidazoline, which may be incorporated in certain instances, include those having a structure according to the general formula provided below:

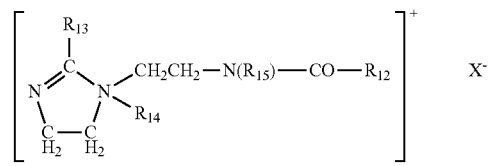

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 (1-methyl-2-norstearyl-3-stearinoacid-amidoethyl-dihydro-imidazolinium methosulfate) by the company Rewo.

Examples of quaternary diammonium or triammonium salt, which may be incorporated in certain instances, include those having a structure in accordance with the following general formula:

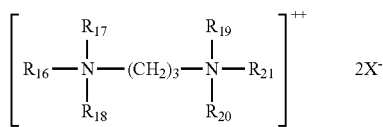

in which $R_{16}$ denotes an alkyl radical comprising approximately from 16 to 30 carbon atoms, which is optionally hydroxylated and/or interrupted with one or more oxygen atoms; $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms; and $X^-$ is an anion chosen from the group of halides, acetates, phosphates, nitrates and methyl sulfates. Such compounds are, for example, FINQUAT CT-P (Quaternium 89), sold by the company Finetex, and FINQUAT CT (Quaternium 75), sold by the company Finetex.

Examples of cationic/cationizable surfactants, which may be incorporated in certain instances, include those having a structure in accordance with the general formula provided below:

R4-A-R5-B wherein R4 is a saturated or unsaturated, straight or branched alkyl chain with 8 to 24 C atoms, R5 is a straight or branched alkyl chain with 1 to 4 C atoms, A is selected from:

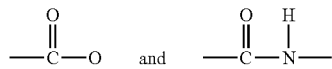

and B is selected from:

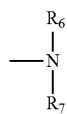

wherein $R_6$ and $R_7$ are the same or different and are H or an alkyl chain with 1 to 4 C atoms, hydroxyl alkyl chain with 1 to 4 C atoms and di hydroxyl alkyl chain with 2 to 4 C atoms,

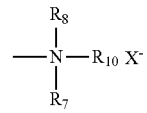

$R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24 C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines, preferably, fatty dialkylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

In an embodiment, cosmetic composition may be formulated with a cationic surfactant chosen from behentrimonium chloride, cetrimonium chloride, behentrimonium methosulfate, or mixtures thereof.

The cosmetic composition may be formulated such that the two or more cationic surfactants are associated with the same or different balancing anionic ions. For example, at least one of the two or more cationic surfactants may have a chloride ion and/or a sulfate ion. In some instances, the two or more cationic surfactants comprise cetrimonium chloride and one or both of behentrimonium methosulfate and behentrimonium chloride. In further instances, the two or more cationic surfactants comprise behentrimonium chloride and one or both of behentrimonium methosulfate and cetrimonium chloride.

In yet another instance, the cationic surfactant(s) is chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof.

Fatty Compound(s)

The cosmetic compositions include one or more fatty compound(s) in amount that my vary, but is typically about 0.1 to about 20 wt. %, based on the total weight of the cosmetic compositions. In some instances, the amount of fatty compounds present in the cosmetic compositions is about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 20 wt.

%, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, about 5 to about 7 wt. %, or about 5 to about 6 wt. %, including all ranges and sub-ranges therebetween, based on the total weight of the cosmetic composition.

Examples of fatty compound(s) that may be incorporated into the cosmetic composition include fatty alcohol, a fatty ester, a fatty ether, a fatty acid, a wax, an oil, a derivative thereof, and a mixture thereof. Additional examples of fatty compounds that are worth mentioning include oils, mineral oil, alkanes (paraffins), fatty alcohol derivatives, fatty acid derivatives, esters of fatty alcohols, hydroxy-substituted fatty acids, waxes, triglyceride compounds, lanolin, and a mixture thereof.

Fatty Ester(s)

The cosmetic compositions may include one or more fatty compound(s) that is a fatty ester. For example, the fatty compound(s) may be chosen from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from $C_{14-15}$ dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

Additionally or alternatively, the fatty ester chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisostearyl dimer dilinoleate, diisostearyl fumarate, and a mixture thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

Fatty Alcohol(s)

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Ether(s)

The fatty compounds may be chosen from fatty ethers. For example, the cosmetic composition may include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, dodecyl ether, dilauryl ether, dimyristyl ether, diisononyl ether, or a mixture thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

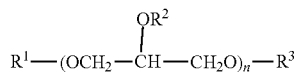

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Wax(es)

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Oil(s)

In some instances, the fatty compounds may include or be chosen from one or more oil(s). Suitable oils include, but are not limited to, synthetic oils such as silicone oils; natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the cosmetic compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Polyol(s)

Optionally, the cosmetic compositions include one or more polyols. The amount of polyol(s) present in the cosmetic composition typically ranges from about 20 wt. % or more, based on the total weight of the cosmetic composition. For example, the amount of polyol(s) in the cosmetic composition may be about 20 to about 87 wt. %, about 20 to about 85 wt. %, about 20 to about 80 wt. %, about 20 to about 75 wt. %, about 20 to about 70 wt. %, about 20 to about 65 wt. %, about 20 to about 60 wt. %, about 20 to about 55 wt. %, about 20 to about 50 wt. %, about 20 to about 45 wt. %, about 20 to about 40 wt. %, about 20 to about 35 wt. %, about 20 to about 30 wt. %; about 30 to about 87 wt. %, about 30 to about 85 wt. %, about 30 to about 80 wt. %, about 30 to about 75 wt. %, about 30 to about 70 wt. %, about 30 to about 65 wt. %, about 30 to about 60 wt. %, about 30 to about 55 wt. %, about 30 to about 50 wt. %, about 30 to about 45 wt. %, about 30 to about 40 wt. %; about 40 to about 87 wt. %, about 40 to about 85 wt. %, about 40 to about 80 wt. %, about 40 to about 75 wt. %, about 40 to about 70 wt. %, about 40 to about 65 wt. %, about 40 to about 60 wt. %, about 40 to about 55 wt. %, about 40 to about 50 wt. %; about 50 to about 87 wt. %, about 50 to about 85 wt. %, about 50 to about 80 wt. %, about 50 to about 75 wt. %, about 50 to about 70 wt. %, about 50 to about 65 wt. %, about 50 to about 60 wt. %; about 60 to about 87 wt. %, about 60 to about 85 wt. %, about 60 to about 80 wt. %, about 60 to about 75 wt. %, about 60 to about 70 wt. %; about 65 to about 87 wt. %, about 65 to about 85 wt. %, about 65 to about 80 wt. %, about 65 to about 75 wt. %; about 70 to about 87 wt. %, about 70 to about 85 wt. %, about 70 to about 75 wt. %, including all ranges and sub-ranges therebetween, based on the total weight of the cosmetic composition.

The term "polyol" should be understood as meaning, within the meaning of the present disclosure, an organic molecule comprising at least two free hydroxyl groups. The polyols of the cosmetic composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the cosmetic composition, in certain instances, include ethylene glycol, propylene glycol, butylene glycol, hexylene glycol, glycerin, diglycerin, diethylene glycol, and dipropylene glycol, polyethylene glycols, and mixtures thereof. In some cases, the polyol is propylene glycol. In some further cases, the polyol is one or both of propylene glycol and butylene glycol. Additionally, in some cases, the cosmetic composition comprises at least propylene glycol, and optionally one or more polyols other than propylene glycol.

Non-limiting examples of polyols that may, optionally, be included in the cosmetic include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In some cases, the one or more polyols may include or are chosen from ethylene glycol, propylene glycol, butylene glycol, hexylene glycol, pentylene glycol, 1,3-propanediol, diethylene glycol, dipropylene glycol, 1,4-butanediol, 1,5-pentanediol, hexane-1,6-diol, glycerin, diglycerin, caprylyl glycol, and a mixture thereof.

Thickening Agent(s)

The cosmetic compositions described herein may, optionally, include a thickening agent. The amount of thickening agents can vary but is typically from about 0.01 to about 20 wt. %, based on the total weight of the cosmetic composition. In some instances, the amount of fatty compounds present in the cosmetic compositions is about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, about 5 to about 7 wt. %, or about 5 to about 6 wt. %, including all ranges and sub-ranges therebetween, based on the total weight of the cosmetic composition.

The thickening agent(s) may be chosen from xanthan gum, guar gum, biosaccharide gum, cellulose, acacia seneca gum, sclerotium gum, agarose, pechtin, gellan gum, hyaluronic acid. Additionally, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/$C_{10-30}$ alkyl acrylate crosspolymer. In some cases, the composition includes ammonium polyacryloyldimethyl taurate and/or sodium polyacrylate. Suitable thickening agents may be found in U.S. patent application Ser. No. 16/731,654, which is incorporated herein, in its entirety for all purposes.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the cosmetic compositions of the instant disclosure. Thickening agents may be referred to as "thickeners" or "viscosity modifying agents." Thickening agents are typically included to increase the viscosity of the cosmetic compositions. Nonetheless, in some instances, certain thickening agents provide additional, surprising benefits to the cosmetic compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

Carboxylic Acid or Carboxylate Based Homopolymer or Co-Polymer, which can be Linear or Crosslinked:

These polymers contain one or more monomers derived from acrylic acid, substituted acrylic acids, and salts and esters of these acrylic acids (acrylates) and the substituted acrylic acids.

Other suitable carboxylic acid or carboxylate polymeric agents include copolymers of acrylic acid and alkyl C5-C10 acrylate, copolymers of acrylic acid and maleic anhydride, and polyacrylate crosspolymer-6.

Another suitable carboxylic acid or carboxylate polymeric agent includes acrylamidopropyltrimonium chloride/acrylates copolymer, a cationic acrylates copolymer (or a quaternary ammonium compound).

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Polyquaternium Compounds:

Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and Co-Polymers:

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. In some instances, PVP and PVP/VA copolymer are preferred.

Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

Polyglyceryl esters:

Non-limiting polyglycerol esters of fatty acids (polygylceryl esters) include those of the following formula:

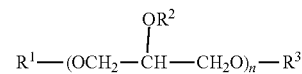

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of non-ionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

Gums:

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

Water-Soluble Solvent(s)

The cosmetic compositions may include one or more water-soluble solvents. The amount of water-soluble solvents in the cosmetic composition, if present, may range from about 1 to about 35 wt. %, based on the total weight of the cosmetic composition. For example, the cosmetic composition may include water-soluble solvents in an amount of about 1 to about 35 wt. %, about 1 to about 30 wt. %, about 1 to about 25 wt. %, about 1 to about 20 wt. %, about 1 to about 18 wt. %, about 1 to about 16 wt. %, about 1 to about 14 wt. %, about 1 to about 12 wt. %, about 1 to about 10 wt. %; about 5 to about 35 wt. %, about 5 to about 30 wt. %, about 5 to about 25 wt. %, about 5 to about 20 wt. %, about 5 to about 18 wt. %, about 5 to about 16 wt. %, about 5 to about 14 wt. %, about 5 to about 12 wt. %, about 5 to about 10 wt. %; about 10 to about 35 wt. %, about 10 to about 30 wt. %, about 10 to about 25 wt. %, about 10 to about 20 wt. %, about 10 to about 18 wt. %, about 10 to about 16 wt. %, about 10 to about 14 wt. %; about 12 to about 35 wt. %, about 12 to about 30 wt. %, about 12 to about 25 wt. %, about 12 to about 20 wt. %, about 12 to about 18 wt. %, about 12 to about 16 wt. %; about 14 to about 35 wt. %, about 14 to about 30 wt. %, about 14 to about 25 wt. %, about 14 to about 20 wt. %, about 14 to about 18 wt. %; about 16 to about 35 wt. %, about 16 to about 30 wt. %, about 16 to about 25 wt. %, about 16 to about 20 wt. %; about 18 to about 35 wt. %, about 18 to about 30 wt. %, about 18 to about 25 wt. %, or about 18 to about 20 wt. %, including ranges and subranges thereof, based on the total weight of the cosmetic composition.

The term "water-soluble solvent" is interchangeable with the term "water-miscible solvent" and means a compound that is liquid at 25°C and at atmospheric pressure (760 mmHg), and it has a solubility of at least 50% in water under these conditions. In some cases, the water-soluble solvent has a solubility of at least 60%, 70%, 80%, or 90%. Non-limiting examples of water-soluble solvents include, for example, glycerin, alcohols (for example, $C_{1-30}$, $C_{1-15}$, $C_{1-10}$, or $C_{1-4}$ alcohols), organic solvents, polyols (polyhydric alcohols), glycols (e.g., butylene glycol, caprylyl glycol, etc.), and a mixture thereof.

In some cases, the water-soluble solvent is a monoalcohol. Non-limiting examples of monoalcohols include ethanol, propanol, butanol, pentanol, hexanol, isopropyl alcohol, cyclohexanol, isobutyl alcohol, 2-methyl-2-butanol (2-methylbutan-2-ol), and a mixture thereof. In some instances, the monoalcohols comprise or are chosen from ethanol, propanol, butanol, pentanol, an isomer thereof, or a combination thereof. In further instances, the one or more monoalcohol(s) includes or consists of ethanol.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. The water-soluble solvents may be organic solvents that can be volatile or non-volatile compounds.

Further non-limiting examples of water-soluble solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Silicone(s)

The cosmetic composition includes silicone(s) typically in an amount ranging from about 0.1 to about 10 wt. %, based on the total weight of the cosmetic composition. For example, the amount of silicone(s) present in the cosmetic composition may range from about 0.1 to about 10 wt. %, about 0.1 to about 8 wt. %, about 0.1 to about 6 wt. %, about 0.1 to about 4 wt. %, about 0.1 to about 3 wt. %; about 0.2 to about 10 wt. %, about 0.2 to about 8 wt. %, about 0.2 to about 6 wt. %, about 0.2 to about 4 wt. %, about 0.2 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including ranges and sub-ranges therebetween, based on the total weight of the cosmetic composition.

The term "amino-functionalized silicone" or "amino silicones" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

Non-limiting examples of silicones include amine-functionalized silicones (e.g., amodimethicone), dimethicone, bis-aminopropyl dimethicone, trimethyl silylamodimethicone, dimethicone copolyols, etc. The cosmetic composition may include, in some instances, one or more silicones chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof. For example, the one or more silicones may be or include one or more dimethicone copolyols. The copolyols may be chosen from Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and a mixture thereof.

The silicone(s) may, optionally, include or be chosen from a siloxane with a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

In some cases, the silicones, optionally, include or are chosen from siloxanes having an organo functional group, such as polyalkylsiloxanes, where at least one alkyl radical is different than methyl, for example organopolysiloxanes having the INCI name Stearyl Dimethicone, Cetyl Dimethicone or $C_{26-28}$ Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone.

In some instances, an amino-functionalized silicones is selected from compounds having the following formula:

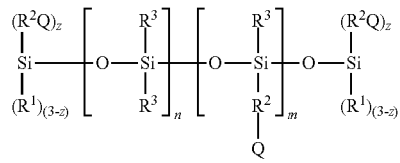

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from $-NR^4_2$ and $-NR^4(CH_2)_xNR^4_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydroxy. Preferred $R^2$ divalent alkylene radicals include trimethylene, tetramethylene, pentamethylene, $-CH_2CH(CH_3)CH_2-$ and $-CH_2CH_2CH(CH_3)CH_2-$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicine has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds of the following formula:

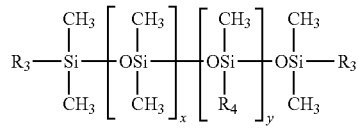

wherein $R^3$ is hydroxyl or $OR_5$, $R_5$ is a $C_1$ to $C_4$ alkyl group, $R^4$ is a group with structure according to the following formula:

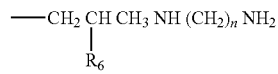

$R_6$ is a $C_1$ to $C_4$ alkyl, n is a 1 to 4, x is the same as "n" described above, and y is the same as "m" described above.

The silicone may be a polysiloxane corresponding to the following formula:

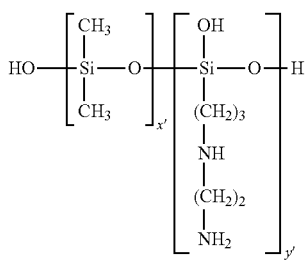

in which x' and y' are integers such that the weight-average molecular weight (Mw) is comprised between about 5000 and 500 000;

b) amino silicones corresponding to following formula:

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula —CqH2qL in which q is a number ranging from 2 to 8 and L is an optionally quaternized amino group chosen from the following groups:

—NR"-Q-N(R")$_2$
—N(R")$_2$
—N+(R")$_3$A–
—N+H(R")$_2$A–
—N+H$_2$(R")A–
—N(R")-Q-N+R"H$_2$A–
—NR"-Q-N+(R")$_2$HA–
—NR"-Q-N+(R")$_3$A–, in which R", which may be identical or different, denote hydrogen, phenyl, benzyl, or a saturated monovalent hydrocarbon-based radical, for example a $C_1$-$C_{20}$ alkyl radical; Q denotes a linear or branched $C_rH_{2r}$ group, r being an integer ranging from 2 to 6, preferably from 2 to 4; and A– represents a cosmetically acceptable ion, in particular a halide such as fluoride, chloride, bromide or iodide.

Another group of amino silicones corresponding to this definition is represented by silicones having the following formula:

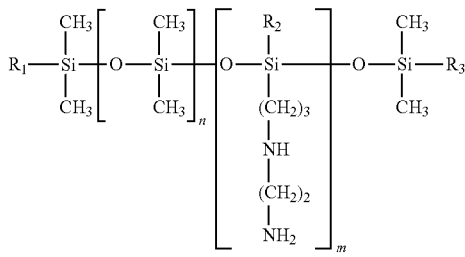

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical. The hydroxy/alkoxy mole ratio ranges preferably from 0.2:1 to 0.4:1 and preferably from 0.25:1 to 0.35:1 and more particularly equals 0.3:1. The weight-average molecular weight (Mw) of the silicone ranges preferably from 2,000 to 1,000,000, more particularly from 3,500 to 200,000.

Another group of amino silicones corresponding to this definition is represented by the following formula:

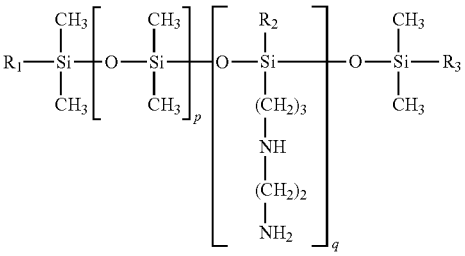

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which may be the same or different, represent a hydroxy or $C_1$-$C_4$ alkoxy radical, where at least one of the radicals $R_1$ or $R_2$ denotes an alkoxy radical.

The alkoxy radical is preferably a methoxy radical. The hydroxy/alkoxy mole ratio ranges generally from 1:0.8 to 1:1.1 and preferably from 1:0.9 to 1:1 and more particularly equals 1:0.95.

Another group of amino silicones is represented by the following formula:

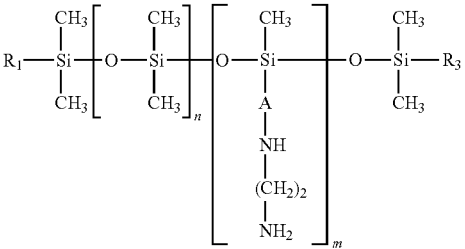

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

Another group of amino silicones is represented by the following formula:

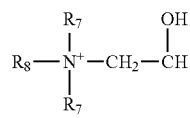

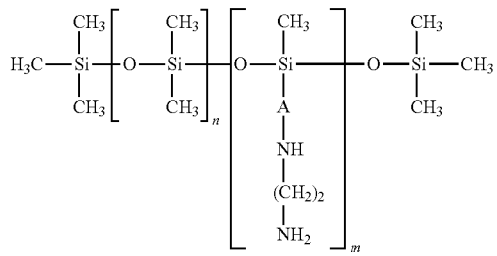

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

Another group of amino silicones is represented by the following formula:

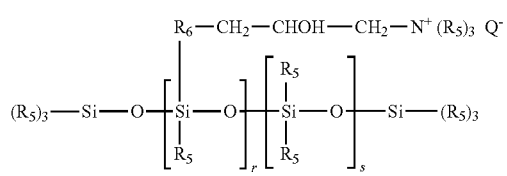

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q– is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in U.S. Pat. No. 4,185,087.

A group of quaternary ammonium silicones is represented by the following formula:

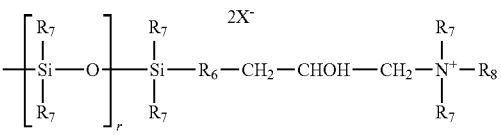

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

X– is an anion such as a halide ion, in particular chloride, or an organic acid salt (for example acetate);

r represents a mean statistical value from 2 to 200 and in particular from 5 to 100. These silicones are described, for example, in patent application EP-A 0530974.

A group of quaternary ammonium silicones is represented by the following formula:

(J)

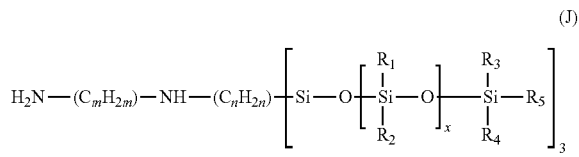

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

multiblock polyoxyalkylenated amino silicones, of type (AB)n, A being a polysiloxane block and B being a polyoxyalkylenated block containing at least one amine group.

Said silicones are preferably constituted of repeating units having the following general formulae:

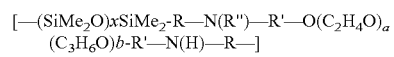

or alternatively

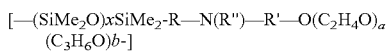
[—(SiMe$_2$O)xSiMe$_2$-R—N(R")—R'—O(C$_2$H$_4$O)$_a$(C$_3$H$_6$O)b-]

in which:
- a is an integer greater than or equal to 1, preferably ranging from 5 to 200, more particularly ranging from 10 to 100;
- b is an integer comprised between 0 and 200, preferably ranging from 4 to 100, more particularly between from 5 and 30;
- x is an integer ranging from 1 to 10 000, more particularly from 10 to 5000; R" is a hydrogen atom or a methyl;
- R, which may be identical or different, represent a divalent linear or branched C$_2$-C$_{12}$ hydrocarbon-based radical, optionally including one or more heteroatoms such as oxygen; preferably, R denotes an ethylene radical, a linear or branched propylene radical, a linear or branched butylene radical, or a —CH$_2$CH$_2$CH$_2$OCH(OH)CH$_2$— radical; preferentially R denotes a —CH$_2$CH$_2$CH$_2$OCH(OH)CH$_2$— radical;
- R', which may be identical or different, represent a divalent linear or branched C$_2$-C$_{12}$ hydrocarbon-based radical, optionally including one or more heteroatoms such as oxygen; preferably, R' denotes an ethylene radical, a linear or branched propylene radical, a linear or branched butylene radical, or a —CH$_2$CH$_2$CH$_2$OCH(OH)CH$_2$— radical; preferentially R' denotes —CH(CH$_3$)—CH$_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2. The weight-average molecular weight (Mw) of the silicone oil is preferably comprised between 5000 and 1,000,000, more particularly between 10,000 and 200,000.

The silicone may be selected from those having at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, and mixtures thereof. In an embodiment, the one or more silicone oils of the present disclosure is a non-amino silicone oil such as a dimethicone.

Non-limiting examples of amino-functionalized silicones include bis-hydroxy/methoxy amodimethicones, bis-cetearyl amodimethicone, amodimethicone, bis(C$_{13-15}$ alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is OCH$_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company. A non-limiting example of amodimethicone products containing amino silicones having structure (D).

The silicone(s) in the cosmetic compositions of the instant disclosure are included in the form of a silicone emulsion comprising at least one silicone and at least one surfactants, for example, nonionic surfactants, cationic surfactants, amphoteric surfactants, anionic surfactants. The silicone emulsions can be nanoemulsions, microemulsions or macroemulsions. Suitable examples of nonionic surfactants are alkoxylated fatty alcohols or polyethylene glycol ethers of mixtures of C8-C30 fatty alcohols with an average of number of moles of ethylene oxide such as C11-15 Pareth-7, laureth-9, laureth-12, deceth-7, deceth-10, trideceth-6, trideceth-10, trideceth-12, or a mixture thereof. Suitable examples of amphoteric surfactants are cocamidopropyl betaine, coco-betaine, or a mixture thereof. Suitable examples of cationic surfactants are quaternary ammonium compounds such as behentrimonium chloride, cetrimoinium chloride, behentrimonium methosulfate, or a mixture thereof. Suitable examples of anionic surfactants are sulfate-based compounds such as further comprises up to 5 wt. % of a surfactant, for example, sodium (or ammonium) lauryl sulfate, sodium (or ammonium) laureth sulfate, or mixtures thereof.

Cationic Polymer(s)

The cosmetic compositions may, optionally, include one or more cationic polymers. The amount of cationic polymers in the cosmetic composition typically ranges from about 0.1 to about 10 wt. % of the total weight of the cosmetic composition. In some instances, the cationic polymers are in an amount ranging from about 0.1 to about 10 wt. %, about 0.1 to about 8 wt. %, about 0.1 to about 6 wt. %, about 0.1 to about 4 wt. %, about 0.1 to about 3 wt. %; about 0.2 to about 10 wt. %, about 0.2 to about 8 wt. %, about 0.2 to about 6 wt. %, about 0.2 to about 4 wt. %, about 0.2 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including ranges and sub-ranges therebetween, based on the total weight of the cosmetic composition.

The cationic polymers can comprise mixtures of monomer units derived from amine- and/or quaternary ammonium-substituted monomer and/or compatible spacer monomers. Suitable cationic polymers include, for example: copolymers of 1-vinyl-2-pyrrolidine and 1-vinyl-3-methylimidazolium salt (e.g., chloride salt) (referred to as Polyquaternium-16); copolymers of 1-vinyl-2-pyrrolidine and dimethylaminoethyl methacrylate (referred to as Polyquaternium-11); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic polymers that may be used include polysaccharide polymers, such as cationic cellulose derivatives and cationic starch derivatives such as polyquaternium-10 and polyquaternium-24. Additionally, or alternatively, the cationic conditioning polymers may include or be chosen from cationic guar gum derivatives, such as guar hydroxypropyltrimonium chloride.

The cosmetic composition may include or be chosen from polyquerniums. For example, the cosmetic composition may include Polyquaternium-1 (ethanol, 2,2',2''-nitrilotris-, polymer with 1,4-dichloro-2-butene and N,N,N',N'-tetramethyl-2-butene-1,4-diamine), Polyquaternium-2, (poly[bis (2-chloroethyl) ether-alt-1,3-bis[3-(dimethylamino)propyl] urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In some instances, the cosmetic compositions of the instant disclosure include one or more cationic polymers selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquerniums, and a mixture thereof. For example, the cationic polymer(s) may be selected from polyquerniums, for example, polyquerniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquerniums can be useful.

In one instance, the one or more cationic polymers is chosen from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof.

Nonionic Surfactant(s)

The cosmetic compositions may, optionally, include one or more nonionic surfactants. The amount of nonionic surfactants, if present, typically range from about 0.05 to about 6 wt. % of the total weight of the cosmetic composition. For example, the total weight of the plurality of nonionic surfactants may range from about 0.05 to about 6 wt. %, 0.05 to about 5 wt. %, 0.05 to about 4 wt. %, 0.05 to about 3 wt. %; from 0.1 to about 6 wt. %, 0.1 to about 5 wt. %, 0.1 to about 4 wt. %, 0.1 to about 3 wt. %; from 0.5 to about 6 wt. %, 0.5 to about 5 wt. %, 0.5 to about 4 wt. %, 0.5 to about 3 wt. %; from 0.8 to about 6 wt. %, 0.8 to about 5 wt. %, 0.8 to about 4 wt. %, 0.8 to about 3 wt. %; from 1 to about 6 wt. %, 1 to about 5 wt. %, 1 to about 4 wt. %, or 1 to about 3 wt. %, including ranges and sub-ranges therebetween, based on the total weight of the cosmetic composition.

Examples of nonionic surfactants that may, in some cases, be suitably incorporated into the cosmetic composition include and/or may be chosen from alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mole of ethylene oxide; ethoxylated oils from plant origin; fatty acid esters of sucrose; fatty acid esters of polyethylene glycol; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

As glyceryl esters of fatty acids, glyceryl stearate (glyceryl mono-, di- and/or tristearate) (INCI name: glyceryl stearate) or glyceryl ricinoleate and mixtures thereof can be cited. As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Additionally or alternatively, the nonionic surfactants may comprise or be selected from alkanolamides, polyglucosides, sorbitan derivatives (not including the hydration of sorbitan to derive sorbitol), and polyol esters.

Alkanolamide(s)

Non-limiting examples of alkanolamides include fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides may include those formed by reacting an alkanolamine and a $C_6$-$C_{36}$ fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA.

Fatty acid alkanolamides include those of the following structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof); wherein $R_5$ is selected from —$CH_2OH$, —$CH_2CH_2OH$, —$CH_2CH_2CH_2OH$, —$CH_2(CHOH)_4CH_2OH$, -benzyl, and mixtures thereof; and wherein $R_6$ is selected from —H, —$CH_3$, —$CH_2OH$, —$CH_2CH_3$, —$CH_2CH_2OH$, —$CH_2CH_2CH_2OH$, —$CH_2(CHOH)_4CH_2OH$, -benzyl, and mixtures thereof.

In some instances, the one or more of the fatty acid alkanolamides include one or more acyl glucamides, e.g., acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide Alkyl Polyglucoside(s)

In some embodiments, the one or more alkyl polyglucosides include those chosen from lauryl glucoside, octyl glucoside, decyl glucoside, coco glucoside, caprylyl/capryl glucoside, sodium lauryl glucose carboxylate, and a mixture thereof. In some cases, the alkyl polyglucosides includes or is chosen from lauryl glucoside. Additionally or alternatively, the alkyl polyglucosides may be chosen from glycerol ($C_6$-$C_{24}$)alkylpolyglycosides including, e.g., polyethoxylated fatty acid mono or diesters of glycerol ($C_6$-$C_{24}$) alkylpolyglycosides. Additional alkyl polyglucosides that may be suitably incorporated, in some instances, in the cosmetic composition includes alkyl polyglucosides having a structure according to the following formula:

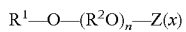

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Useful alkyl poly glucosides may, in some instances, include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

Sorbitan Derivative(s)

Suitable sorbitan derivatives that may be incorporated into the plurality of nonionic surfactants include those chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE (4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate and sorbitan tristearate and a mixture thereof.

Additional and/or alternative sorbitan derivatives include sorbitan esters including, e.g., esters of $C_{16}$-$C_{22}$ fatty acid and of sorbitan that were formed by esterification, with sorbitol, of at least one fatty acid comprising at least one saturated or unsaturated linear alkyl chain respectively having from 16 to 22 carbon atoms. These esters can be chosen in particular from sorbitan stearates, behenates, arachidates, palmitates or oleates, and their mixtures. Examples of optional sorbitan esters include sorbitan monostearate (INCI name: Sorbitan stearate), sorbitan tristearate, sorbitan monopalmitate (INCI name: Sorbitan palmitate). A preferable sorbitan ester is sorbitan tristearate.

Polyol Ester(s)

Non-limiting examples of polyol esters include those chosen from alkoxylated polyol esters. For instance, the alkoxylated polyol esters may be chosen from pegylated derivatives of propylene glycol oleate, propylene glycol caprylate/caprate, propylene glycol cocoate, propylene glycol stearate, and a mixture thereof. In certain embodiments, the alkoxylated polyol esters are chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof. In some instances, the polyol ester is or includes PEG-55 propylene glycol oleate. Additionally, and/or alternatively, the polyol esters may be chosen from ethoxylated fatty acid esters of sorbitan comprising from 2 to 30 mol of ethylene oxide.

In some cases, the polyol ester may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

Sources of unsaturated polyol esters of glycerol include synthesized oils, natural oils (e.g., vegetable oils, algae oils, bacterial derived oils, and animal fats), combinations of these, and the like. Non-limiting examples of vegetable oils include Abyssinian oil, Almond oil, Apricot oil, Apricot Kernel oil, Argan oil, Avocado oil, Babassu oil, Baobab oil, Black Cumin oil, Black Currant oil, Borage oil, Camelina oil, Carinata oil, Canola oil, Castor oil, Cherry Kernel oil, Coconut oil, Corn oil, Cottonseed oil, Echium oil, Evening Primrose oil, Flax Seed oil, Grape Seed oil, Grapefruit Seed oil, Hazelnut oil, Hemp Seed oil, Jatropha oil, Jojoba oil, Kukui Nut oil, Linseed oil, Macadamia Nut oil, Meadowfoam Seed oil, Moringa oil, Neem oil, Olive oil, Palm oil, Palm Kernel oil, Peach Kernel oil, Peanut oil, Pecan oil, Pennycress oil, Perilla Seed oil, Pistachio oil, Pomegranate Seed oil, Pongamia oil, Pumpkin Seed oil, Raspberry oil, Red Palm Olein, Rice Bran oil, Rosehip oil, Safflower oil, Seabuckthorn Fruit oil, Sesame Seed oil, Shea Olein, Sunflower oil, Soybean oil, Tonka Bean oil, Tung oil, Walnut oil, Wheat Germ oil, High Oleoyl Soybean oil, High Oleoyl Sunflower oil, High Oleoyl Safflower oil, High Erucic Acid Rapeseed oil, combinations of these, and the like. Non-limiting examples of animal fats include lard, tallow, chicken fat, yellow grease, fish oil, emu oil, combinations of these, and the like. Non-limiting example of a synthesized oil includes tall oil, which is a byproduct of wood pulp manufacture. In some embodiments, the natural oil is refined, bleached, and/or deodorized.

The polyol esters may optionally be a natural polyol esters chosen from vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, in one aspect, sucrose, and mixtures thereof.

Additional non-limiting examples of nonionic surfactants that may optionally be used in the cosmetic composition include and/or may be chosen from alkanolamides; polyoxyalkylenated nonionic surfactants; polyglycerolated nonionic surfactants; ethoxylated fatty esters; alcohols, alphadiols, alkylphenols and esters of fatty acids, being ethoxylated, propoxylated or glycerolated; copolymers of ethylene oxide and/or of propylene oxide; condensates of ethylene oxide and/or propylene oxide with fatty alcohols; polyethoxylated fatty amides; ethoxylated oils from plant origin; fatty acid esters of sucrose; fatty acid esters of polyethylene glycol; N—($C_6$-$C_{24}$)alkylglucamine derivatives, amine oxides such as $(C_{10}-C_{14})$alkylamine oxides or N—$(C_{10}-C_{14})$acylaminopropylmorpholine oxides; and mixtures thereof.

pH Adjuster(s)

The cosmetic composition may include one or more pH adjusters to increase or decrease the overall pH of the cosmetic composition. For example, one or more acids may be included to decrease the pH of the cosmetic composition. Examples of suitable acids for decreasing the pH of the cosmetic composition include, but are not limited to, citric acid, acetic acid, and the like. The cosmetic composition may include one or more bases, such as sodium hydroxide, potassium hydroxide and the like, to increase the pH of the cosmetic composition. Additional or alternative acids and bases that are suitable for adjusting the pH of the cosmetic composition are readily known to one of ordinary skill in the art.

The amount of the pH adjuster in the cosmetic composition may be based on the desired pH of the final cosmetic composition and/or product. For example, the cosmetic composition may have an amount of pH adjusters such that the pH of the composition is about 3 to about 7, preferably about 3.5 to about 6.5, preferably about 3.5 to about 6, or preferably about 3.5 to about 5.5.

The amount of the pH adjuster in the cosmetic composition may be based on the desired pH of the final cosmetic composition and/or product. For example, the total amount of the pH adjuster may range from about 0.05 to about 20 wt. %, based on the total weight of the cosmetic composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the cosmetic composition.

Monoalcohol(s)

The cosmetic compositions may, optionally, include monoalcohol(s), such as those having 1 to 10 carbons, preferably, from 2 to 6 carbons. The amount of monoalcohol present in the cosmetic composition may range from about 0.1 to about 10 wt. %, based on the total weight of the cosmetic composition. For example, the amount of monoalcohol present in the cosmetic composition may range from about 0.1 to about 10 wt. %, about 0.1 to about 8 wt. %, about 0.1 to about 6 wt. %, about 0.1 to about 4 wt. %, about 0.1 to about 3 wt. %; about 0.2 to about 10 wt. %, about 0.2 to about 8 wt. %, about 0.2 to about 6 wt. %, about 0.2 to about 4 wt. %, about 0.2 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including ranges and sub-ranges therebetween, based on the total weight of the cosmetic composition The one or more monoalcohols of the cosmetic composition may be chosen from ethanol, propanol, butanol, pentanol, hexanol, isopropyl alcohol, cyclohexanol, isobutyl alcohol, 2-methyl-2-butanol (2-methylbutan-2-ol), and a mixture thereof. In some instances, the monoalcohols comprise or are chosen from ethanol, propanol, butanol, pentanol, an isomer thereof, or a combination thereof. In further instances, the one or more monoalcohol(s) includes or consists of ethanol.

Ester(s)

The cosmetic compositions may optionally include esters, such as ester oils chosen from one or more diester, one or more triglycerides, and mixtures thereof. The amount of diesters present in the cosmetic composition may range from, e.g., about 0.05 to about 4.5 wt. %, about 0.1 to about 4 wt. %, about 0.1 to about 3.5 wt. %, about 0.1 to about 3 wt. %, about 0.5 to about 3 wt. %, about 0.5 to about 2.5 wt. %; about 0.5 to about 2 wt. %, or about 0.5 to about 1.5 wt. %, including all ranges and sub-ranges therebetween, based on the total weight of the cosmetic composition. In certain embodiments, the amount of diesters present in the cosmetic composition is about 0.05. 0.1, 0.15, 0.2, 0.25, 0.3, 0.35, 0.4, 0.45, 0.5, 0.75, 1, 1.25, 1.5, 1.75, 2, 2.25, 2.5, 2.75, 3 wt. %, based on the total weight of the cosmetic composition.

Non-limiting examples of liquid esters include fatty esters from a $C_6$-$C_{32}$ fatty acid and/or a $C_6$-$C_{32}$ fatty alcohol, and are liquid at 25° C., 1 atm. These esters may be liquid esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In some cases, for the esters of monoalcohols, at least one of the alcohol or the acid from which the esters of the invention result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some cases, it is particularly useful to include cetyl esters in the hair conditioning compositions. Cetyl Esters is a mixture of the following esters of saturated fatty acids and fatty alcohols: cetyl palmitate, cetyl stearate, myristyl myristate, myristyl stearate, cetyl myristate, and stearyl stearate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Non-limiting liquid esters (ester oils) or liquid fatty esters that may be mentioned include, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, and shea butter oil.

The esters of the present disclosure may also further comprise solid fatty acid esters and/or fatty acid esters including solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

In an embodiment, the one or more esters of the cosmetic composition of the present disclosure include one or more diesters, in particular, diester oils, chosen from diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisostearyl dimer dilinoleate, diisostearyl fumarate, and mixtures thereof.

Chelating Agent(s)

The cosmetic composition may, optionally, include chelating agents. The amount of chelating agent present in the cosmetic composition may be, e.g., about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 20 wt. %, about 0.25 to about 15 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 20 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 20 wt. %, about 0.75 to about 15 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the cosmetic composition.

Non-limiting examples of chemical chelating agents include aminotrimethyl phosphonic acid, β-alanine diacetic acid, cyclodextrin, cyclohexanediamine tetracetic acid, diethylenetriamine pentamethylene phosphonic acid, diethanolamine N-acetic acid, ethylene diamine tetracetic acid (EDTA or $YH_4$) and its sodium ($YH_3Na$, $Y_2H_2Na_2$, $YHNa_3$ and $YNa_4$), potassium ($YH_3K$, $Y_2H_3K_3$ and $YK_4$), calcium disodium, and diammonium salts and its salts with triethanolamine (TEA-EDTA), etidronic acid, galactanic acid, hydroxyethyl ethylenediamine tetracetic acid (HEDTA) and its trisodium salt, gluconic acid, glucuronic acid, nitrilotriacetic acid (NTA) and its trisodium salt, pentetic acid, phytic acid, ribonic acid, diammonium citrate, disodium azacycloheptane diphosphonate, disodium pyrophoshate, hydroxypropyl cyclodextrin, methyl cyclodextrin, pentapotassium triphosphate, pentasodium aminotrimethylene phosphonate, pentasodium ethylenediamine tetramethylene phosphonate, pentasodium pentetate, pentasodium triphosphate, potassium citrate, potassium EDTMP, sodium EDTMP, sodium chitosan methylene phosphonate, sodium hexametaphosphate, sodium metaphosphate, potassium polyphosphate, sodium polyphosphate, sodium trimetaphosphate, sodium dihydroxyethylglycinate, potassium gluconate, sodium gluconate, sodium glucopeptate, sodium glycereth-1 polyphosphate, tetrapotassium pyrophosphate, triethanolamine polyphosphate (TEA), tetrasodium pyrophosphate, trisodium phosphate, potassium triphosphonomethylene oxide, sodium metasilicate, sodium phytate, sodium polydimethylglycinophenolsulfonate, tetrahydroxyethyl ethylene diamine, tetrahydroxypropyl ethylene diamine, tetrapotassium etidronate, tetrasodium etidronate, tetrasodium iminodisuccinate, trisodium ethylenediamine disuccinate, ethanolamine N,N-diacetic acid, disodium acetate, dimercaprol, deferoxamine, Zylox, and/or iron chelating agent disclosed and claimed in the international patent application WO 94/61338, which is incorporated herein in its entirety for all purposes. Examples of biological chelating agents include metallothionein, transferrin, calmodulin, and sodium chitosan methylene phosphonate.

In at least one instance, the chelating agent is trisodium ethylenediamine disuccinate.

Preservative(s)

Preservatives may be included in the cosmetic composition in an amount typically from about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 7 wt. %, about 0.01 to about 6 wt. %, about 0.01 to about 5 wt. %; about 0.1 to about 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, 0.1 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, or about 4 to about 7 wt. %, including all ranges and sub-ranges therebetween, based on the total weight of the cosmetic composition. Non-limiting examples of preservatives include sodium benzoate, potassium sorbate, phenoxyethanol, salicylic acid, tocopherol, chlorphenesin, BHT, disodium EDTA, pentaerythrityl tetra-di-t-butyl hydroxyhydrocinnamate, and mixtures thereof.

Kits

Aspects of the instant disclosure are directed to kits, which include cosmetic compositions as discussed herein. In an embodiment, the cosmetic compositions of the instant disclosure are hair cosmetic or hair treatment compositions. For example, kits may include at least one cosmetic composition according to the instant disclosure, such as a hair cosmetic and/or hair treatment composition, and one or more additional compositions, such as a shampoo, a conditioner, etc. The various compositions are separately contained in the kits. In some instances, the kits include one or more cosmetic compositions, such as a hair cosmetic and/or hair treatment composition, according to the instant disclosure, a shampoo, a conditioner, a mask, and/or other hair treatment products, all of which are separately contained.

The cosmetic compositions of the kit may be packaged in a variety of different containers, such as, for example, a ready-to-use container. Non-limiting examples of useful packaging include tubes, jars, caps, unit dose packages, and bottles, including squeezable tubes, bottles, and sprayable containers. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a cosmetic composition according to the instant disclosure, and the other tube may include a composition to be used with the cosmetic composition, for example, a shampoo, a conditioner, an all-in-one shampoo/conditioner (i.e., a conditioning shampoo; also referred to as a "co-wash") mask or other cosmetic products.

Method(s) for Producing Cosmetic Compositions

Aspects of the disclosure relate to methods for producing cosmetic compositions. The methods for producing cosmetic compositions typically include:
- (I) producing a deep eutectic solvent system comprising:
  - (a) about 0.1 to about 25 wt. % of citric acid; and
  - (b) about 0.2 to about 40 wt. % of one or more urea compound chosen from dimethyl urea, a hydroxyl ethyl urea, or a combination thereof,
    - wherein a weight ratio of the citric acid of (a) to the urea compound of (b) is 1 or less; and
- (II) adding the deep eutectic solvent system of (I) to a base composition to produce a cosmetic composition.

The method may further include forming the deep eutectic solvent (DES) system of (I) by mixing the citric acid and urea compound(s) in certain ratios, e.g., as discussed herein. In some cases, the DES system may be formed at room temperatures, e.g., when the citric acid and urea compounds mix as liquids at room temperature. In other cases, the method also includes heating a mixture/combination of the citric acid and the urea compound to a temperature of about 70° C. to about 90° C. Heating the mixture/combination of citric acid and urea compounds is typically beneficial when the citric acid and urea compounds do not mix as liquids at room temperature. The mixture/combination of citric acid and urea compounds may be heated to a temperature, such that the citric acid and urea compounds mix as liquids. For instance, the mixture/combination of citric acid and urea compounds may be heated to a temperature of about 75° C. to about 90° C., about 80° C. to about 90° C., about 85° C. to about 90° C., about 70° C. to about 85° C., about 75° C. to about 85° C., about 80° ° C. to about 85° C., about 70° C. to about 80° C., about 75° C. to about 80° C., or about 70° C. to about 75° C., or any ranges or subranges thereof.

The method may include producing a base of the cosmetic composition by combining one or more components, such as fatty compounds, polyols, thickening agents, water-soluble solvents, silicone oils, etc. One of ordinary skill would understand how to combine the foregoing components and/or compound such that the base of the composition is stable and/or uniform. In some cases, the base of the cosmetic composition may be heated, mixed, and/or receive shear forces, e.g., from an emulsifier.

Method(s) for Treating Hair

Aspects of the instant disclosure also relate to methods for using such cosmetic compositions. A method for treating hair according to aspects of the disclosure typically includes:
- (I) optionally, applying a shampoo to hair;
- (II) optionally, rinsing the hair to remove at least a portion of the shampoo;
- (III) applying a cosmetic composition comprising:
  - (a) about 0.1 to about 25 wt. % of citric acid; and
  - (b) about 0.2 to about 40 wt. % of one or more urea compound chosen from dimethyl urea, a hydroxyl ethyl urea, or a combination thereof,
    - wherein a molar ratio of the citric acid of (a) to the urea compound of (b) is 1 or less; and
- (IV) optionally, rinsing the hair to remove at least a portion of the cosmetic composition.

The methods for treating and/or cleaning hair according to the disclosure may vary but typically include applying a cosmetic composition as disclosed herein, allowing the cosmetic composition to remain on the hair for a sufficient amount of time, and rinsing the cosmetic compositions from the hair.

In some instances, however, the cosmetic composition may be a leave-in composition. For example, the cosmetic compositions may allowed to remain on the hair indefinitely, i.e., the cosmetic composition is not removed or rinsed from the hair prior to styling the hair.

The cosmetic composition may be applied to the hair in a sequence with other compositions. For example, the cosmetic composition may be applied to the hair before shampooing the hair, after shampooing the hair, before conditioning the hair, and/or after conditioning the hair, etc. The cosmetic compositions, however, are not required to be used in a sequence.

The cosmetic compositions are useful for conditioning, managing the hair, improving durability, and/or improving the hair's resistance to thermal degradation. The cosmetic compositions can be applied to the wet or damp hair and may be massaged into the hair, for example, with the hands, and/or spread throughout the hair with a comb or brush. This results in a smoothing and softening of the hair, which reduces frizz, dryness, and unwanted volume. Alternatively, the cosmetic composition and extraneous water may be combined, and optionally mixed, prior to application to the body. For example, the cosmetic composition may be combined in a container, bowl, packaging, bottle, etc., and subsequently applied to the body after formation of the opaque emulsion.

In some cases, the cosmetic compositions are used in conjunction with additional hair-care compositions in a routine, for example, during an individual's normal showering/bathing routine. The cosmetic composition may be applied to the hair individually or may be combined with one or more additional compositions. For instance, the cosmetic composition may be mixed with a shampoo (or conditioner) prior to application to the hair. In this case, the mixture of the shampoo (or conditioner) and the cosmetic composition are simultaneously applied to the hair during the cleansing or conditioning process and simultaneously rinsed from the hair. Alternatively, the cosmetic composition may be layered on top of (or lathered into) hair to which a shampoo (or conditioner) has already been applied or vice versa. In this case, the cosmetic composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the cosmetic composition is also applied to the hair.

When used in conjunction with a shampoo and/or a conditioner, the cosmetic composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (cosmetic composition of the instant disclosure:shampoo/conditioner, etc.).

When the cosmetic composition is not being mixed with another composition prior to application to the hair, the cosmetic composition may be applied to the hair immediately after or before the hair is treated with another composition (e.g., a shampoo and/or a conditioner). For example, the cosmetic compositions may be applied to the hair within about a few seconds or 1, 2, 5, 10, or 20 minutes before or after a shampoo and/or a conditioner is applied to the hair.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the hair cleansing compositions of the instant disclosure can be free or essentially free of all components and elements positively recited throughout the instant disclosure. In some instances, the hair cleansing compositions of the present disclosure may be substantially free of non-incidental amounts of the ingredient(s) or compound(s) described herein. A non-incidental amount of an ingredient or compound is the amount of that ingredient or compound that is added into the hair cleansing composition by itself. For example, a hair cleansing composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the hair cleansing composition includes both components (or the composition includes more than two components that overlap), an overlapping compound does not represent more than one component. For example, certain compounds may be characterized as both an emulsifier and a surfactant. If a particular hair composition includes both an emulsifier and a surfactant, the compounds that may be characterized as both an emulsifier and a surfactant will serve only as either the emulsifier or the surfactant—not both.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations. Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as hair on a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

Embodiments of the Disclosure

In certain embodiments, the cosmetic compositions includes:
about 0.1 to about 25 wt. %, preferably about 0.5 to about 20 wt. %, preferably about 1 to about 20 wt. %, of citric acid;
about 0.2 to about 40 wt. %, preferably about 0.2 to about 35 wt. %, more preferably about 0.5 to about 30 wt. %, of one or more urea compound chosen from imidazolidinyl urea, diazolidinyl urea, m-dimethylaminophenyl urea, dimethyl urea, a hydroxyethyl urea, urea, urea derivatives, imidazolidinyl urea, diazolidinyl urea, m-dimethylaminophenyl urea, dimethyl urea, a hydroxyethyl urea, N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(tris-hydroxymethylmethyl)urea; N-ethyl-N'-(2-hydroxyethyl)urea; N,N-bis(2-hydroxyethyl)urea; N,N'-bis(2-hydroxyethyl)urea; N,N-bis(2-hydroxypropyl)urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl).-N',N'-dimethylurea; N,N,N',N'-tetrakis (2-hydroxyethyl)urea; N',N'-bis(2-hydroxyethyl)-N', N'-bis(2-hydroxypropyl)-urea, and a mixture thereof.
wherein a molar ratio of the citric acid of (a) to the urea compound of (b) is 1 or less, preferably about 10:1 to about 0.5:10, more preferably about 1:1 to about 1:3; and
about 20 wt. % or more, preferably about 20 to about 90 wt. %, more preferably about 50 to about 90 wt. %, of water, wherein all weight percentages are based on the total weight of the cosmetic composition.

In additional embodiments, the cosmetic compositions includes:
about 0.1 to about 25 wt. %, preferably about 0.5 to about 20 wt. %, preferably about 1 to about 20 wt. %, of citric acid;
about 0.2 to about 40 wt. %, preferably about 0.2 to about 35 wt. %, more preferably about 0.5 to about 30 wt. %, of one or more urea compound chosen from dimethyl urea, a hydroxyl ethyl urea, or a combination thereof, wherein a molar ratio of the citric acid of (a) to the urea compound of (b) is 1 or less, preferably about 10:1 to about 0.5:10, more preferably about 1:1 to about 1:3; and about 20 wt. % or more, preferably about 20 to about 90 wt. %, more preferably about 50 to about 90 wt. %, of water;

optionally, about 0.1 to about 10 wt. %, preferably about 0.1 to about 8 wt. %, more preferably about 0.2 to about 6 wt. %, of one or more cationic surfactants chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof;

optionally, about 0.1 to about 25 wt. %, preferably about 0.5 to about 18 wt. %, more preferably about 1 to about 16 wt. %, of one or more fatty compounds including, e.g., fatty alcohol, a fatty ester, a fatty ether, a fatty acid, a wax, an oil, a derivative thereof, or a mixture thereof;

optionally, about 20 wt. % or more, preferably about 20 to about 87 wt. %, more preferably about 20 to about 80 wt. %, of a polyol, such as those chosen from ethylene glycol, propylene glycol, butylene glycol, hexylene glycol, glycerin, diglycerin, diethylene glycol, and dipropylene glycol, polyethylene glycols, and mixtures thereof. In some cases, the polyol is propylene glycol;

optionally, about 0.1 to about 20 wt. %, preferably about 0.1 to about 18 wt. %, more preferably about 0.1 to about 14 wt. % of a thickening agent, including, e.g., polyacrylate crosspolymers or crosslinked polyacrylate polymers, cationic acrylate copolymers, anionic acrylic or carboxylic acid polymers, polyacrylamide polymers, polysaccharides, gums, polyquaterniums, vinylpyrrolidone homopolymers/copolymers, C8-24 hydroxy substituted aliphatic acid, C8-24 conjugated aliphatic acid, sugar fatty esters, polyglyceryl esters, or a mixture thereof;

optionally, about 0.1 to about 35 wt. %, preferably about 1 to about 25 wt. %, more preferably about 1 to about 20 wt. %, of a water-soluble solvent, such as alkyl alcohols having 1 to 4 carbon atoms, glycol ethers, 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof;

optionally, about 0.01 to about 20 wt. %, preferably about 0.01 to about 14 wt. %, more preferably about 0.01 to about 7 wt. %, of a preservative such as, e.g., sodium benzoate, potassium sorbate, phenoxyethanol, salicylic acid, tocopherol, chlorphenesin, BHT, disodium EDTA, pentaerythrityl tetra-di-t-butyl hydroxyhydrocinnamate, or a mixture thereof;

optionally, about 0.1 to about 10 wt. %, preferably about 0.1 to about 9 wt. %, more preferably about 0.2 to about 8 wt. %, of a silicone, such as those chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof;

optionally, about 0.01 to about 20 wt. %, preferably about 0.01 to about 15 wt. %, more preferably about 0.1 to about 8 wt. %, of a chelating agent;

optionally, about 0.01 to about 20 wt. % of a pH adjuster, preferably in an amount such that the pH of the composition is about 3 to about 7; and optionally, about 0.001 to about 10 wt. % of a fragrance, wherein all weight percentages are based on the total weight of the cosmetic composition.

In yet further embodiments, a method for producing cosmetic compositions include:

(I) producing a deep eutectic solvent system comprising:
(a) about 0.1 to about 25 wt. %, preferably about 0.5 to about 20 wt. %, preferably about 1 to about 20 wt. %, of citric acid; and
(b) about 0.2 to about 40 wt. %, preferably about 0.2 to about 35 wt. %, more preferably about 0.5 to about 30 wt. %, of one or more urea compound chosen from dimethyl urea, a hydroxyl ethyl urea, or a combination thereof,
wherein a molar ratio of the citric acid of (a) to the urea compound of (b) is 1 or less, preferably about 10:1 to about 0.5:10, more preferably about 1:1 to about 1:3; and (II) adding the deep eutectic solvent system of (I) to a base composition to produce a cosmetic composition.

EXAMPLES

Implementation of the present disclosure is provided by way of the following examples. The following examples serve to elucidate aspects of the technology without being limiting in nature.

Example 1

Three exemplary cosmetic compositions (Exemplary Compositions A-C) were prepared from deep eutectic solvent ("DES") system. The DES system was prepared by mixing citric acid and dimethyl urea to a temperature of about 80° C. to about 85° C. The DES system was then solubilized in distilled water. The formulation for Exemplary Compositions A-C are provided in Table 1, below.

TABLE 1

|  | INCI US Name | Ex. A | Ex. B | Ex. C |
| --- | --- | --- | --- | --- |
| Citric Acid | CITRIC ACID | 0.6 wt. % | 2 wt. % | 18 wt. % |
| Urea | DIMETHYL UREA | 0.9 wt. % | 3 wt. % | 27 wt. % |
| Water | WATER | Q.S. to 100 | Q.S. to 100 | Q.S. to 100 |
| Mole ratio of citric acid to urea compound |  | 1:3 | 1:3 | 1:3 |
| Weight ratio of citric acid to urea compound |  | 2:3 | 2:3 | 2:3 |

Example 2

Exemplary Compositions B and D was applied to hair swatches and evaluated in comparison to the application of only a conventional sulfate-based shampoo (the control). Exemplary Composition D had the same formulation as Exemplary Composition B, except that a DES system was not formed from the citric acid and dimethyl urea before preparing the cosmetic composition.

Natural brown wavy Caucasian hair swatches (medium curls), were washed with a conventional sulfate-based shampoo and rinsed before the application of Exemplary Compositions B and D. An amount of 0.4 gram of each of Exemplary Compositions B and D per gram of hair swatch was massaged onto their respective hair swatches for 1 minute, left on the hair swatches for another minute, rinsed for 30 seconds, and then blow dried for 2 minutes. These hair swatches were then evaluated to assess the effects of Exemplary Compositions B and D using a rinse-off procedure. The control was prepared according to the above procedure, except that a cosmetic composition was not applied to the hair swatch after the conventional sulfate-based shampoo.

Additional hair swatches were prepared by applying Exemplary Compositions B and D to hair swatches, in an amount of 0.15 grams of composition per gram of respective hair swatches. Specifically, Exemplary Compositions B and D were massaged onto their respective hair swatches for one minute, left on the hair swatches for a minute, and then below dried for two minutes. These hair swatches were evaluated to assess the effects of Exemplary Compositions B and D using a leave-on procedure.

Anti-frizz properties or the degree of frizz on each of the hair swatches was evaluated using imaging analysis. Anti-frizz properties of the hair swatches were evaluated after the hair swatches were blow dried, and after 1 hour, after 2 hours, after 4 hours, after 8 hours, after 12 hours, and after 24 hours of the hair swatches residing in a humidity chamber at 80% relative humidity and room temperature.

Figure 2:
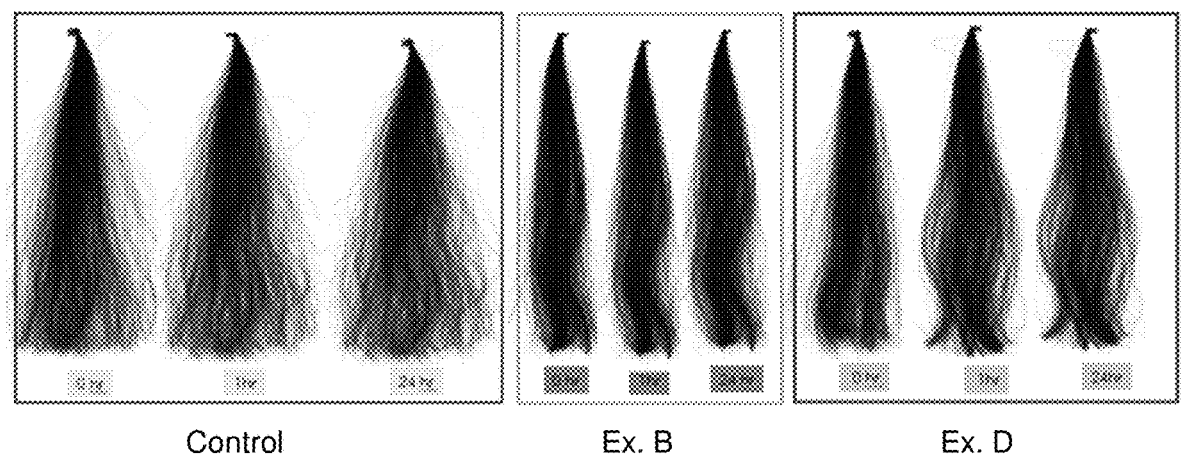

FIG. 1 provides images of the hair swatches treated with Exemplary Compositions B and D and the control using the rinse out procedure. FIG. 2 provides images of the hair swatches treated with Exemplary Compositions B and D and the control using the leave-on procedure. As seen in FIGS. 1 and 2, Exemplary Compositions B and D provided significantly better anti-frizz properties to the control hair swatches. Further, Exemplary Compositions B and D provided better hair volume control. Exemplary Composition B provides surprisingly better volume control than Exemplary Composition D and the control, as shown in Table 2.

TABLE 2

| STD Effective Volume | 0 H | 1 H | 2 H | 4 H | 8 H | 12 H | 24 H |
|---|---|---|---|---|---|---|---|
| Control | 20.54 | 11.55 | 11.22 | 11.21 | 11.42 | 11.39 | 11.38 |
| Ex. B (Rinse-out) | 12.6 | 9.45 | 9.9 | 10.11 | 10.16 | 10.18 | 10.29 |
| Ex. D (Rinse-out) | 12.65 | 12.24 | 12.68 | 12.22 | 12.19 | 12.1 | 12.03 |
| Ex. B (Leave-in) | 6.36 | 4.83 | 5.27 | 5.73 | 5.8 | 5.7 | 5.58 |
| Ex. D (Leave-in) | 10.24 | 11.54 | 11.8 | 11.92 | 11.99 | 12.03 | 12.07 |

Example 3

Hair swatches treated with exemplary Compositions A and C were evaluated and compared to hair swatches treated only with a conventional sulfate-based shampoo (the Control). Hair swatches were washed with a conventional sulfate-based shampoo and rinsed before the application of Exemplary Compositions A and C in an amount of 0.15 grams of composition per gram of respective hair swatches. The compositions were massaged onto their respective hair swatches for one minute, left on the hair swatches for a minute, and then below dried for two minutes. The control was prepared according to the above procedure, except that a cosmetic composition was not applied to the hair swatch after the conventional sulfate-based shampoo.

These hair swatches were evaluated to assess the effects of Exemplary Compositions A and C using a leave-on procedure. The hair swatches underwent cyclic fatigue using a Cyclic Tester to determine the durability of the hair swatch. The Cyclic Tester simulates every day hair grooming by subjecting a set number of fibers to repeated cyclic tensile deformations until failure. Additionally, the hair swatches were evaluated for the thermal denaturation temperature, which is associated with cross-link density of the amorphous matrix, using Differential Scanning calorimetry. Differential scanning calorimetry measures the thermal stability of hair's major morphological components.

Figure 3:
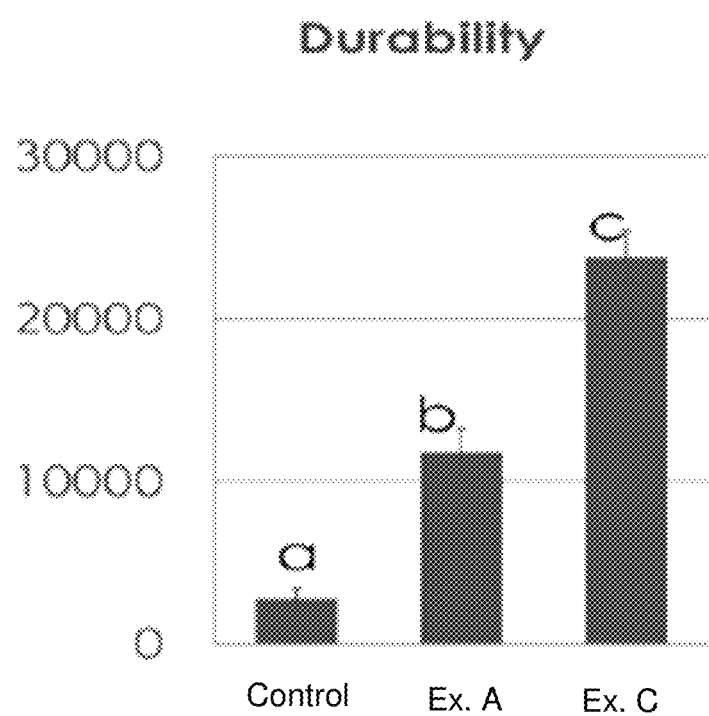
FIG. 3 is a bar graph showing the durability of hair swatches after treatment with exemplary cosmetic compositions according to aspects of the disclosure.
Figure 4:
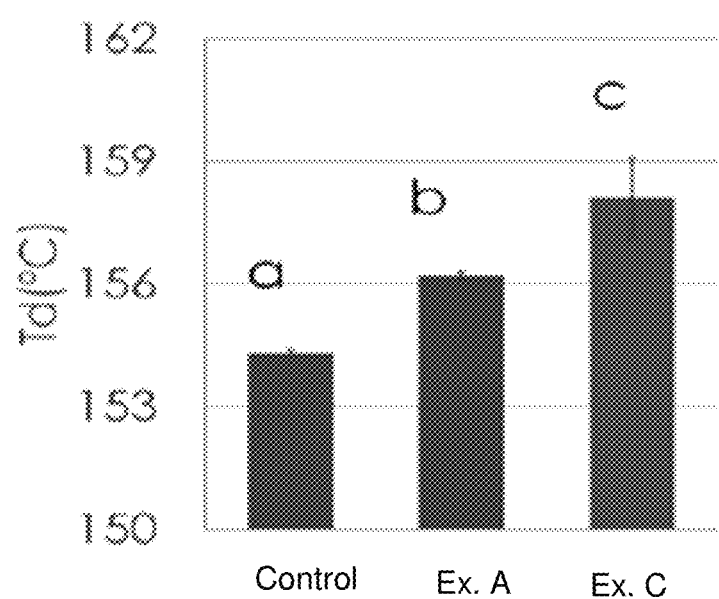
FIG. 4 is a bar graph showing the denaturation temperature of hair swatches after treatment with exemplary cosmetic compositions in accordance with aspects of the disclosure.
Figure 5:
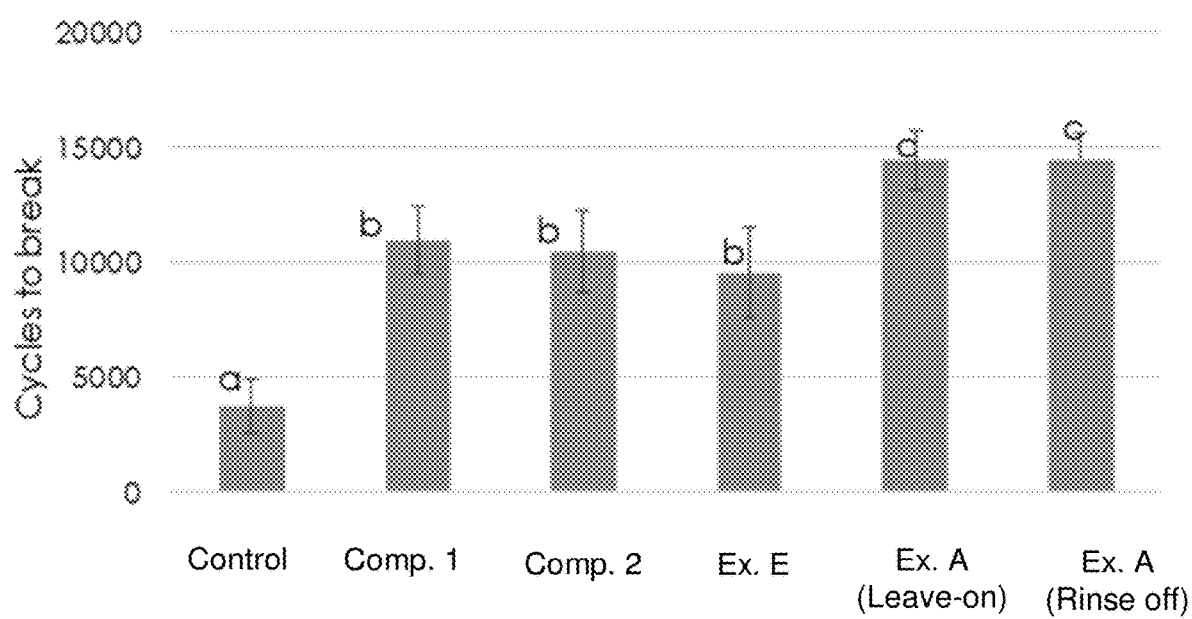
FIG. 5 is a bar graph showing the durability of hair swatches after treatment with comparative compositions and exemplary cosmetic composition according to aspects of the disclosure.
Figure 6:
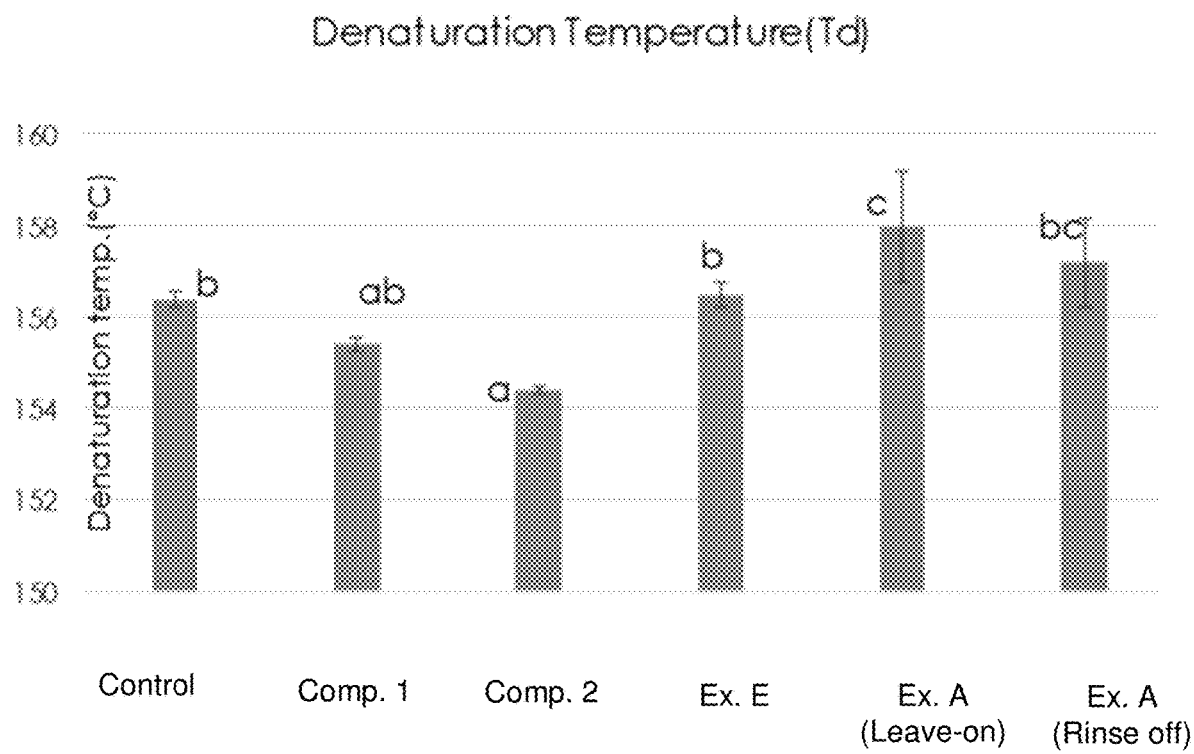
FIG. 6 is a bar graph showing the denaturation temperature of hair swatches after treatment with comparative compositions and exemplary cosmetic composition in accordance with aspects of the disclosure.
Figure 7:
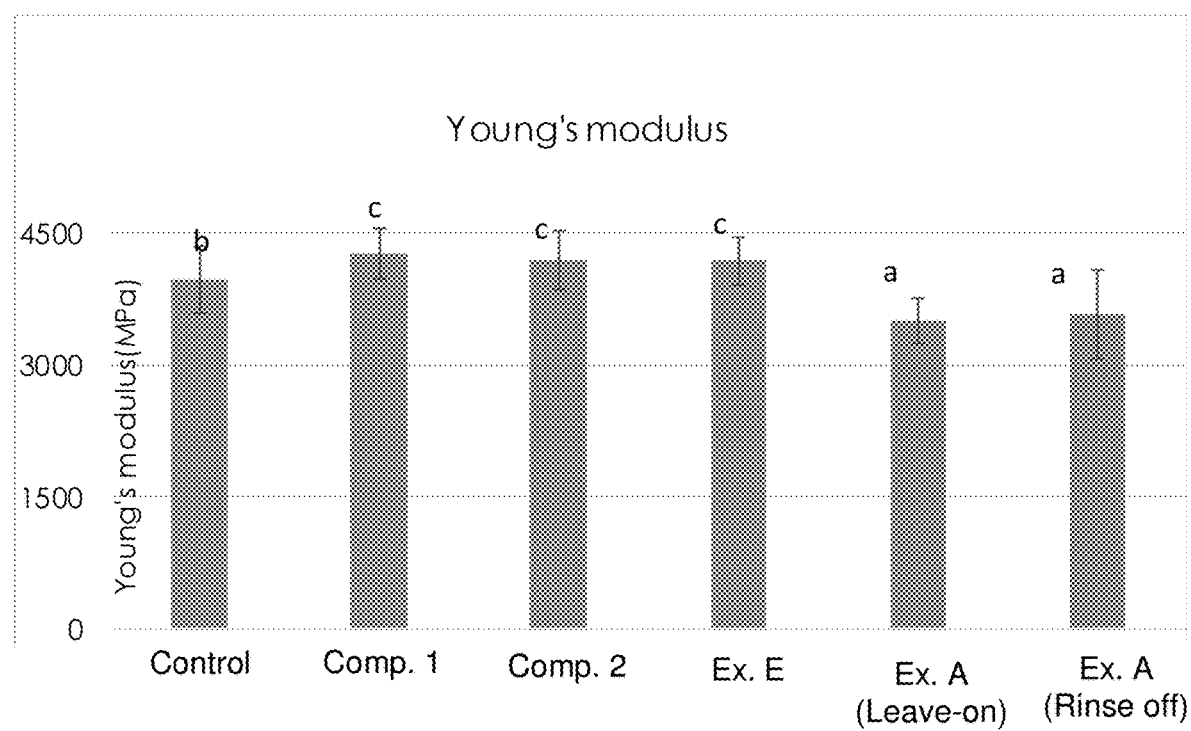
FIG. 7 is a bar graph showing the Young's modulus of hair swatches after treatment with comparative compositions and exemplary cosmetic composition according to aspects of the disclosure.
Figure 8:
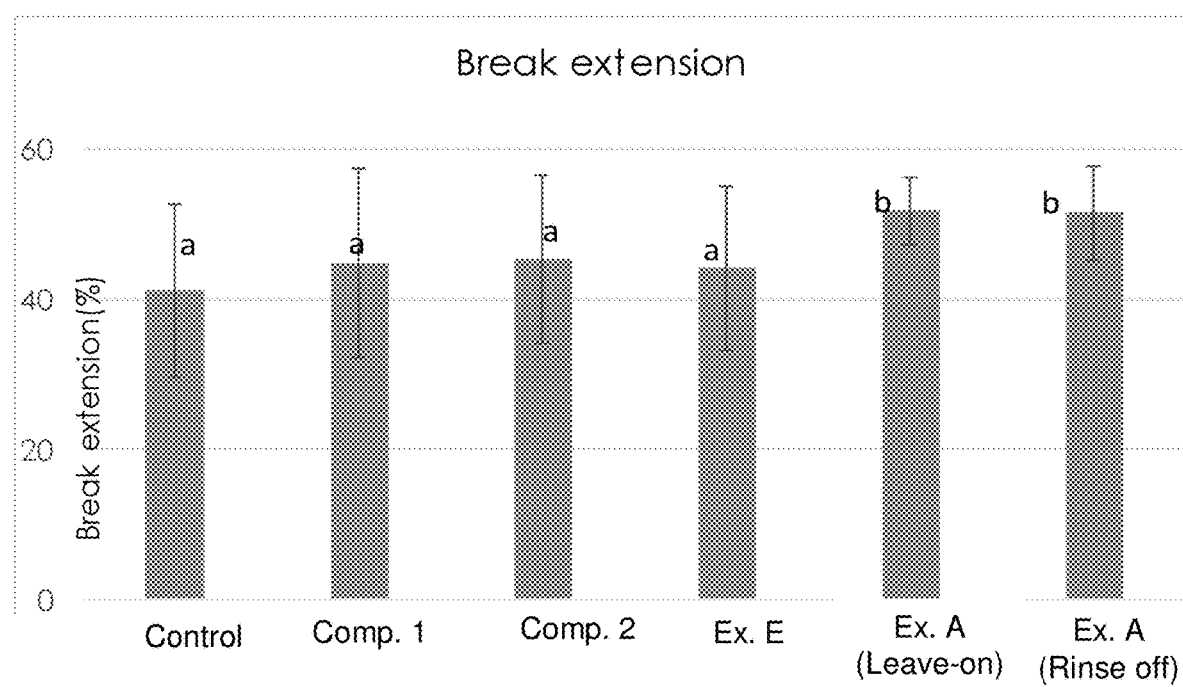
FIG. 8 is a bar graph showing the break extension of hair swatches after treatment with comparative compositions and exemplary cosmetic composition in accordance with aspects of the disclosure.

As seen in FIGS. 3 and 4, the hair swatch treated with Exemplary Compositions C exhibited significantly better durability and denaturation temperature than the control hair swatch. The hair swatch treated with Exemplary Compositions A also exhibited improved durability and denaturation temperature than the control hair swatch.

Example 4

Hair swatches treated with Exemplary Composition A and E and Comparative Compositions 1 and 2 were evaluated in comparison to the hair swatches treated with only a conventional sulfate-based shampoo (the control). Exemplary Composition E had the same formulation as Exemplary Composition A, except that a DES system was not prepared from the citric acid and dimethyl urea before preparing the cosmetic composition. The formulations for Comparative Compositions 1 and 2 are provided in Table 3.

TABLE 3

|  | INCI US Name | Comp. 1 | Comp. 2 |
|---|---|---|---|
| Citric Acid | CITRIC ACID | 0.6 wt. % |  |
| Urea | DIMETHYL UREA |  | 0.9 wt. % |
| Water | WATER | Q.S. to 100 | Q.S. to 100 |

An amount of 0.4 gram of each of Exemplary Composition A and E and Comparative Compositions 1 and 2 per gram of hair swatch was massaged onto their respective hair swatches for 1 minute, left on the hair swatches for another minute, rinsed for 30 seconds, and then blow dried for 2 minutes. These hair swatches were then evaluated to assess the effects of Exemplary Composition A and E and Comparative Compositions 1 and 2 using a rinse-off procedure. The control was prepared according to the above procedure, except that a cosmetic composition was not applied to the hair swatch after the conventional sulfate-based shampoo.

An additional hair swatch was treated with an amount of 0.15 grams of Exemplary Composition A per gram of the hair swatch. Exemplary Composition A was massaged onto the respective hair swatch for one minute, left on the hair swatch for a minute, and then below dried for two minutes. The hair swatch was evaluated to assess the effects of Exemplary Composition A using a leave-on procedure.

The hair was then assessed to evaluate the effect of Exemplary Composition A and E on the thermal denaturation temperature (which corresponds to cross-link density), durability of the hair, the Young's modulus, and the break extension as compared to the effects of Comparative Compositions 1 and 2 and the Control. The thermal denaturation temperature and durability of the hair was determined as discussed in Example 2.

The hair treated with the rinse off and leave-on procedures with Exemplary Composition A exhibited significantly better durability as measured by break cycles, and better denaturation temperature. For example, the hair treated with Exemplary Composition A exhibited an increase durability of about 40% compared to Comparative Compositions 1 and 2. Similarly, the break extension and Young's modulus of the hair treated with Exemplary Composition A were better than the break extension of the hair treated with Comparative Compositions 1 or 2. FIGS. 5-8 are graphs of the break cycles, denaturation temperature, Young's modulus, and break extension of the hair treated with Exemplary Composition A and E in comparison to Comparative Compositions 1 and 2 and the control.

What is claimed is:

1. A cosmetic composition comprising:
   (a) about 0.1 to about 25 wt. % of citric acid;
   (b) about 0.2 to about 40 wt. % of hydroxylethyl urea,
      provided that the citric acid of (a) and the hydroxylethyl urea of (b) are in a molar ratio of about 1:1 to about 1:4 ((a):(b)),
      an amount of the citric acid of (a) and an amount of the hydroxylethyl urea of (b) are included as a deep eutectic solvent consisting of the amount of the citric acid of (a) and the amount of the hydroxylethyl urea of (b), and
      the cosmetic composition comprises 1 wt. % or more of the deep eutectic solvent; and
   (c) at least 20 wt. % of water,
      wherein all weight percentages are based on the total weight of the cosmetic composition.

2. The cosmetic composition of claim 1 comprising at least 5 wt. % of the deep eutectic solvent.

3. The cosmetic composition of claim 1 comprising:
   (a) about 1.5 to about 25 wt. % of the citric acid; and
   (b) about 2.5 to about 40 wt. % of the hydroxylethyl urea.

4. The cosmetic composition of claim 1 comprising:
   (a) about 15 to about 25 wt. % of the citric acid; and
   (b) about 20 to about 40 wt. % of the hydroxylethyl urea.

5. The cosmetic composition of claim 1 further comprising:
   (d) about 0.1 to about 10 wt. % of one or more cationic surfactants chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamidopropyidiethylamine, arachidamidoethyidiethylamine, arachidamidoethyidimethylamine, and mixtures thereof.

6. The cosmetic composition of claim 1 further comprising:
   (e) about 0.1 to about 25 wt. % of one or more fatty compounds chosen from a fatty alcohol, a fatty ester, a fatty ether, a fatty acid, a wax, an oil, a derivative thereof, and a mixture thereof.

7. The cosmetic composition of claim 1 further comprising:
   (f) about 20 wt. % or more of a polyol chosen from ethylene glycol, propylene glycol, butylene glycol, hexylene glycol, pentylene glycol, diethylene glycol, dipropylene glycol, 1,3 propanediol, glycerin, polyethylene glycols, and a mixture thereof.

8. A cosmetic composition consisting of:
   (a) about 0.1 to about 25 wt. % of citric acid;
   (b) about 0.2 to about 40 wt. % of hydroxylethyl urea,
      provided the citric acid of (a) and the hydroxylethyl urea of (b) are in a molar ratio of about 1:1 to about 1:4 ((a):(b)),
      an amount of the citric acid of (a) and an amount of the hydroxylethyl urea of (b) are included as a deep eutectic solvent consisting of the amount of the citric acid of (a) and the amount of the hydroxylethyl urea of (b), and
      the cosmetic composition comprises 1 wt. % or more of the deep eutectic solvent; and
   (c) about 20 wt. % or more of water;
   (d) about 0.1 to about 10 wt. % of one or more cationic surfactants;
   (e) about 0.1 to about 25 wt. % of one or more fatty compounds;
   (f) about 20 wt. % or more of a polyol;
   (g) optionally, about 0.1 to about 20 wt. % of a thickening agent;
   (h) about 0.1 to about 35 wt. % of a water-soluble solvent;
   (i) optionally, about 0.01 to about 20 wt. % of a preservative;
   (j) optionally, about 0.1 to about 10 wt. % of a silicone;
   (k) optionally, about 0.01 to about 20 wt. % of a chelating agent;
   (l) optionally, about 0.01 to about 20 wt. % of a pH adjuster; and
   (m) optionally, about 0.001 to about 10 wt. % of a fragrance,
      wherein all weight percentages are based on the total weight of the cosmetic composition.

9. A cosmetic composition prepared by
   (I) forming a deep eutectic solvent consisting of:
      (a) citric acid; and
      (b) hydroxyl ethyl urea,
         provided the citric acid of (a) and the hydroxylethyl urea of (b) are in a molar ratio of about 1:1 to about 1:4 ((a):(b)),
   (II) adding the deep eutectic solvent of (I) to a base composition to produce a cosmetic composition comprising at least 1 wt. % of the deep eutectic solvent, provided the cosmetic composition comprises;
      (a) about 0.1 to about 25 wt. % of citric acid;
      (b) about 0.2 to about 40 wt. % of hydroxylethyl urea; and
      (c) at least 20 wt. % of water.

10. The cosmetic composition of claim 9 comprising at least 5 wt. % of the deep eutectic solvent.

11. A method for treating hair comprising:
   (I) optionally, applying a shampoo to hair;
   (II) optionally, rinsing the hair to remove at least a portion of the shampoo;

(III) applying the cosmetic composition of claim 1 to the hair; and
(IV) optionally, rinsing the hair to remove at least a portion of the cosmetic composition.

\* \* \* \* \*